(12) United States Patent
Mukoh et al.

(10) Patent No.: US 9,625,380 B2
(45) Date of Patent: Apr. 18, 2017

(54) OPTICAL COHERENCE TOMOGRAPHY WITH HOMODYNE-PHASE DIVERSITY DETECTION

(71) Applicant: HITACHI, LTD., Tokyo (JP)

(72) Inventors: Masaki Mukoh, Tokyo (JP); Tatsuro Ide, Tokyo (JP); Kentaro Osawa, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 14/904,208

(22) PCT Filed: Sep. 4, 2013

(86) PCT No.: PCT/JP2013/073741
§ 371 (c)(1),
(2) Date: Jan. 11, 2016

(87) PCT Pub. No.: WO2015/033394
PCT Pub. Date: Mar. 12, 2015

(65) Prior Publication Data
US 2016/0153904 A1    Jun. 2, 2016

(51) Int. Cl.
*G01B 9/02* (2006.01)
*G01N 21/47* (2006.01)
(52) U.S. Cl.
CPC ..... *G01N 21/4795* (2013.01); *G01B 9/02081* (2013.01); *G01B 9/02091* (2013.01); *G01B 2290/70* (2013.01)
(58) Field of Classification Search
CPC ............ G01N 21/4795; G01B 9/02081; G01B 9/02091; G01B 2290/70
See application file for complete search history.

(56) References Cited

U.S. PATENT DOCUMENTS

| 6,377,349 | B1 | 4/2002 | Fercher |
| 2008/0067321 | A1 | 3/2008 | Miyamoto et al. |
| 2015/0049343 | A1* | 2/2015 | Shaked ............. G01B 9/02057 356/503 |

FOREIGN PATENT DOCUMENTS

| JP | 11-325849 A | 11/1999 |
| JP | 2004-028970 A | 1/2004 |
| JP | 4564948 B2 | 10/2010 |

OTHER PUBLICATIONS

International Search Report of PCT/JP2013/073741.
(Continued)

*Primary Examiner* — Hwa Lee
(74) *Attorney, Agent, or Firm* — Mattingly & Malur, PC

(57) ABSTRACT

There is provided an optical tomographic observation device which has a resolving power which is higher than those of a conventional optical tomographic observation device and a confocal microscope by a simple configuration by applying a homodyne phase diversity detection technology and designing so as to satisfy the following formula when λ is a wavelength of a laser light source, Δλ is a wavelength half width at half maximum, NA is a numerical aperture of an objective optical element, S is an effective area of a photodetector, and M is a detection magnification of a detection surface relative to a condensing surface.

$$\frac{1}{NA^2} \le \frac{k_1}{0.886} \frac{\lambda}{\Delta\lambda}$$

$$\frac{\lambda}{\left(NA\sqrt{1-NA^2}\right)} \le 0.901 \sqrt{\frac{S}{M^2}}$$

$$0.441 \le k_1 \le 0.750$$

12 Claims, 22 Drawing Sheets

(56) References Cited

OTHER PUBLICATIONS

A technical monthly publication, O plus E, 2009, pp. 636-639, vol. 31.
E. Beaurepaire et al., "Full-field optical coherence microscopy", Optics Letters, Feb. 15, 1998, pp. 244-246, vol. 23, No. 4.
M. Akiba et al., "Full-field optical coherence tomography by two-dimensional heterodyne detection with a pair of CCD cameras", Optics Letters, May 15, 2003, pp. 816-818, vol. 28, No. 10.

\* cited by examiner

*FIG. 19*

|  | FIG. 17 | FIG. 18 |
|---|---|---|
| BEAM EXPANDER CONVERSION SYSTEM | KEPLERIAN TYPE | GALILEAN TYPE |
| BEAM MAGNIFICATION FOR ENLARGEMENT | X10 | X10 |
| LENS 1 FOCAL LENGTH f1 (mm) | 10 | -10 |
| LENS 2 FOCAL LENGTH f2 (mm) | 100 | 100 |
| BEAN EXPANDER FULL LENGTH L(mm) | 110 | 90 |

OPTICAL COHERENCE TOMOGRAPHY WITH HOMODYNE-PHASE DIVERSITY DETECTION

TECHNICAL FIELD

The present invention concerns an optical tomographic observation method and an optical tomographic observation device, and relates to an optical observation technology which can visualize a distribution of an inspection substance object in an optical tomographic direction.

BACKGROUND ART

Recently, Optical Coherence Tomography (OCT) which forms images indicating a surface form and an internal form of an object to he measured by using light beams from a laser light source and so forth attracts attention. Since the OCT does not have such invasiveness to the human body that an X-ray CT has, development of application thereof, in particular, in the medical field and the biological field is expected. For example, in the field of ophthalmology, a device for forming images of the eyeground, the cornea and so forth enters into the stage of practical application. In the OCT, a signal is obtained by bifurcating light from a light source into signal light with which a measurement object is to be irradiated and reference light which is reflected by a reference light mirror without irradiating the measurement object with it, multiplexing the signal light which is light reflected from the measurement object and the reference light, and making them mutually interfere.

The OCT is roughly divided into a Time-domain OCT and a Fourier-domain OCT depending on a method of scanning a measurement position in its optical axis direction (hereinafter, referred to as a z-scan). FIG. 1 is a schematic diagram of an optical system of the Time-domain OCT. In this system, the z scan of a measurement object 104 is performed by using a low coherence light source as a light source 101 and scanning a reference light mirror 102 as shown by an arrow 103 at measurement. Thereby, only a component which is included in signal light 105 and matches reference light 106 in optical path length interferes with it and a detection signal as shown in FIG. 2 is obtained from a detector 107. A desired signal as shown in FIG. 3 is demodulated by performing envelope detection on the signal shown in FIG. 2.

On the other hand, the Fourier-domain OCT is further divided into a Swept-source OCT and a spectral-domain OCT. In the Swept-source OCT, the z can is performed by using a wavelength sweeping type light source which can sweep the wavelength of light to be emitted as the light source and sweeping the wavelength of the light source at measurement, and the desired signal is obtained by Fourier-converting wavelength dependency (an interference spectrum) of the intensity of detected interference light. In the spectral-domain OCT, to diffract generated interference light by a spectroscope and to detect the intensity of the interference light (the interference spectrum) of each wavelength component by using a wide bandwidth light source as the light source corresponds to performing the z scan. The desired signal is demodulated by Fourier-converting the obtained interference spectrum.

In the conventional OCT devices as mentioned above, a spatial resolving power in a depth direction is determined by a spectral width of the light source, and heightening of the resolving power has been promoted by widening the spectral width.

In addition, there is a need for speeding-up aiming at biometry, and measurement in a z-axis direction is sped up by realizing mirror drive-less in the abovementioned Fourier-domain OCT (Patent Literature 1). In addition, in speeding-up in x y axis directions, there is a plane bulk acquiring technology using a surface light source which is called a "full-fielding" technology, and a Polarization Sensitive OCT device which utilizes the full-fielding technology is also proposed (Patent Literature 2).

In addition, as an optical tomographic observation device which is already used in the field of bio-imaging, a confocal laser microscope is known. The confocal laser microscope is a kind of the microscope which can reconstruct an image of high resolution and three-dimensional information, and has a characteristic that a distortion-free image can be obtained even from a thick sample having such a complicated structure that a plurality of reflection surfaces are present. A plurality of pieces of data on observation images which have been picked up at every minute point are reconfigured by a computer and thereby a three-dimensional whole image is acquired.

As the theoretical and greatest characteristic of the confocal microscope, a confocal optical system can be given. In the confocal optical system, a point light source is projected onto a sample and, further, a pin hole and a detector (mostly, a photomultiplier tube) are arranged at a re-imaging position of the sample which is called a detection surface. Here, since all of the point light source, the sample, and the pin hole (an imaging surface position) are at conjugated positions, it is called the confocal optical system. By taking such a configuration, when a sample observation image which is at a certain lens position, that is, in a certain focal length state is to be acquired, since light reflected from different depths of focus is cut (light-shielded) by the pin hole arranged on the confocal optical system, the distortion-free image can be acquired. On the other hand, since in a general optical microscope, also the light reflected from the different depths of focus is incident upon the detector together therewith, a distorted image is made. Optical tomographic observation becomes possible by acquiring the image at each focal length by using the confocal optical system and reconstructing a result of observation at the plurality of focal lengths on a computer (Non-Patent Literature 1).

CITATION LIST

Patent Literature

Patent Literature 1: JP H11(1999)-325849 A
Patent Literature 2: JP 2004-028970 A
Non-Patent Literature
Non-Patent Literature 1: A technical monthly publication, O plus E, Vol. 31 (2009), pp. 636-639

SUMMARY OF INVENTION

Technical Problem

There are problems as follows in the abovementioned conventional OCT devices. In any of the OCT devices, coherence of the light source is dominant over a vertical resolving power in optical tomographic observation, a broadband light source becomes necessary in order to realize a high vertical resolving power, and it induces enlargement of the light source and higher price of the light source. Further, due to use of the broadband light source, when an objective lens and so forth have been used in order to obtain a high plane resolving power, problems of chromatic aberration and so forth are induced and therefore it is difficult to form a minute spot. Further, in the Fourier-domain OCT aiming at speeding-up, not only the light source but also a high-speed signal source for performing the z scan or the spectroscope for receiving light from the broadband light source are needed. Since all of them are costly and large-sized, there is a problem that the OCT device itself becomes costly and large-sized.

In addition, in the full-field OCT microscope in Patent Literature 2 aiming at speeding-up, a reference mirror is scanned four times in wavelength order of light in order to acquire information in the depth direction and then signal analysis (fitting for structural estimation) is needed for every pixel on each CCD detector. Therefore, it was difficult to realize dramatic speeding-up when a time for data processing was included. Moreover, optical coherence of the light source is dominant over the vertical resolving power of the device similarly to the conventional OCT devices, having the same problem.

On the other hand, in the confocal microscope, there are such problems that in order to construct the confocal optical system including the pin hole, not only high alignment accuracy of respective components is required but also the entire device becomes large-sized. In particular, an effective detection area which is a region not light-shielded by the pin hole is dominant over the vertical resolving power of the confocal microscope. Since, in order to improve the vertical resolving power, it is important to make the effective detection area small, that is, to make the size of the pin hole small, not only the abovementioned problem becomes more difficult at that time but also a detected light amount itself becomes small. Accordingly, it is necessary to increase a measurement time, that is, a cumulative time of detected light in order to obtain the sufficient detected light amount.

Although, in the foregoing, the problems have been described by focusing on speeding-up, there also exists a low resolution observation method which makes high-speed measurement possible by reducing measurement points as a countermeasure thereto in these devices. However, in any event, it is obvious that it is difficult for the prior art to simultaneously satisfy speeding-up and heightening of resolution.

The present invention has the following first object and second object in view of such circumstances. The first object of the present invention is to provide an optical tomographic observation device having a high resolving power in x, y, z directions, that is, in three dimensions and a simple configuration. The second object of the present invention is to provide a full-field type optical tomographic observation device having a high vertical resolving power.

Solution to Problem

The inventors of the present invention have found out that the homodyne phase diversity detection technology (Japanese Patent No. 4564948) utilizing an interference phenomenon of light is a useful technology also in optical tomographic observation.

Further, the inventors of the present invention have found that the optical tomographic observation using this homodyne-phase diversity detection (in the present specification, hereinafter, referred to as HOCT) has superiority to the optical-axis direction, that is, the vertical resolving power in three-dimensional high-magnification observation by satisfying predetermined conditions, even in comparison with not only the conventional OCT but also the confocal microscope through which three-dimensional observation of an observation substance is possible similarly.

Further, since they have found out a configuration that the high vertical resolving power can be realized by contrivance on a photodetector also in regard to the HOCT (a full-field HOCT) by surface detection which aims at speeding-up of three-dimensional observation, description will be made continuously.

In the following, the HOCT of the present invention, the conventional OCT and the confocal microscope will be studied in simple models shown in FIG. 4 to FIG. 6.

FIG. 4 is a schematic diagram showing a configuration of the conventional OCT device. A light beam emitted from a low coherence light source 4101 is made into collimated light by a collimate lens 4102 and is split into signal light and reference light by a beam splitter (BS). The configuration is made such that the signal light is made to irradiate the sample therewith and the other reference light is reflected by a mirror 4103 placed in another optical path and they are finally subjected to light interference on a photodetector 4104.

FIG. 5 is a schematic diagram showing a configurational example of the HOCT device of the present invention. The light beam emitted from a light source 4201 is made into the collimated light by a collimate lens 4202 and is split into the signal light and the reference light by the beam splitter. The signal light is converged by an objective lens 4205 so as to irradiate the sample therewith and the reference light is made incident upon a mirror 4203 placed in another optical path. The configuration that the signal light and the reference light are finally subjected to light interference by a detection unit 4204 is the same as that of the conventional OCT. However, it is greatly different in the points that even when the light 4201 used is a high coherence light source, there is no problem, and that the detection unit 4204 is configured by a polarization interference optical system and the photodetector which are called homodyne-phase diversity detection. Incidentally, a polarization beam splitter (PBS) is placed on an optical path branch and a ¼ wavelength plate (QWP) is partially placed in order to make it match the polarization interference optical system of the detection unit and there exist optical systems using the similar components also in the conventional OCT devices.

FIG. 6 is a schematic diagram showing a configuration of a general confocal microscope device. The light beam emitted from a light source 4301 is made into the collimated light by a collimate lens 4302 and is converged onto the sample by an objective lens 4305. Light fed back from the sample is detected by a photodetector 4304 through an objective lens 4305 and a detection lens 4306. Although, here, an optical system (an infinite system) using the collimated light has been shown for easy comparison, it is also possible to configure the same confocal optical system in an optical system (a finite system) which has used convergent-divergent light. One big difference from the configuration in FIG. 5 is that a light shield which is called a pin hole 4307 is arranged on a detection surface of the photodetector 4304 and reflected, scattered light other than that from a focal surface of an observation sample is made so as not to enter the photodetector 4304 by the pin hole 4304.

A result that the vertical resolving powers in the respective systems have been estimated by using the three models will be shown in the following. A case where the signal light is condensed onto the measurement object by an objective optical element (a condensing lens) and the measurement object has a flat reflection surface in the vicinity of a focal point is considered. Incidentally, an actual observation substance may be thought as an aggregate having the plurality of reflection surfaces in a direction of a depth of focus. Here, it is supposed that z is a position (displaced from a focal position) in the optical axis direction of the objective optical element, in consideration of the influence from one reflection surface.

(A) Vertical Resolving Power in HOCT

A signal $I_{HOCT}$ obtained by the HOCT is as in the following formula (A-1).

$$I = \int_D |E_s||E_r|\cos(\phi_s - \phi_r)\,dr \quad [\text{A-1}]$$

$$Q = \int_D |E_s||E_r|\sin(\phi_s - \phi_r)\,dr$$

Here, r=(x, y) is a coordinate vector of a light beam section, D denotes a detection region and $\int_D dr$ means an integration operation of the whole area in the light beam. In addition, subscripts s and r denote the signal light (signal) and the reference light (reference). $\phi_s$ is a signal light wave surface and $\phi_r$ denotes a reference light wave surface. Since the reference light is simply reflected by the mirror, the wave surface can be regarded to be in an ideal state (aberration-free) and is set as $\phi_r=0$. In addition, for simplicity, it is supposed that distributions of intensity (magnetic field amplitude) of the signal light and the reference light in the light beam are flat. At this time, the formula (A-1) is simplified to the following formula (A-2).

$$I = |E_s||E_r|\int_D \cos(\phi_s)\,dr \quad [\text{A-2}]$$

$$Q = |E_s||E_r|\int_D \sin(\phi_s)\,dr$$

When the reflection surface of the measurement object is displaced from the focal position of the objective lens, the signal light wave surface $\phi_s$ has a defocus aberration. Since the signal light wave surface $\phi_s$ is reciprocally influenced by defocus, ignoring higher-order components over the tertiary one which are small in absolute value, it can be described by the following formula (A-3).

$$\phi_s = W_{00} + W_{20}r^2\,[\lambda] \quad [\text{A-3}]$$

$$W_{00} = 2 \cdot \frac{z}{\lambda}$$

$$W_{20} = 2 \cdot \frac{z}{2\lambda}NA^2 = \frac{z}{\lambda}NA^2$$

Here, when simplifying the integral terms of cos and sin in the formula (A-2), the following formulae (A-4) and (A-5) are obtained by using sinc(x)=sin(x)/x.

$$\int_D \cos(\phi_s)\,dr = \int_0^{2\pi}d\theta\int_0^1 \rho\cos 2\pi(W_{00}+W_{20}\rho^2)\,d\rho \quad [\text{A-4}]$$

$$= \pi\mathrm{sinc}(\pi W_{20})\cdot\cos 2\pi\left(W_{00}+\frac{W_{20}}{2}\right)$$

$$\int_D \sin(\phi_s)\,dr = \int_0^{2\pi}d\theta\int_0^1 \rho\sin 2\pi(W_{00}+W_{20}\rho^2)\,d\rho \quad [\text{A-5}]$$

$$= \pi\mathrm{sinc}(\pi W_{20})\cdot\sin 2\pi\left(W_{00}+\frac{W_{20}}{2}\right)$$

The signal $I_{HOCT}$ obtained by the HOCT can be expressed by the formula (A-6) by using the above formulae (A-2), (A-4) and (A-5) and the formula ($I_{HOCT}=\sqrt{(I^2+Q^2)}$) showing the phase diversity detection.

$$I_{HOCT}^2 = |E_s|^2|E_r|^2\left[\begin{array}{l}\left\{\pi\mathrm{sinc}(\pi W_{20})\cdot\sin 2\pi\left(W_{00}+\frac{W_{20}}{2}\right)\right\}^2 + \\ \left\{\pi\mathrm{sinc}(\pi W_{20})\cdot\cos 2\pi\left(W_{00}+\frac{W_{20}}{2}\right)\right\}^2\end{array}\right] \quad [\text{A-6}]$$

$$= \pi^2|E_s|^2|E_r|^2\mathrm{sinc}\left(\pi\cdot\frac{z}{\lambda}NA^2\right)$$

Here, when the vertical resolving power is defined by Full Width at Half Maximum (FWHM), the FWHM the vertical direction in the HOCT can be expressed by the following formula (A-7).

$$\mathrm{sinc}^2\left(\pi\cdot\frac{z}{\lambda}NA^2\right) \le \frac{1}{2} \quad [\text{A-7}]$$

$$\therefore FWHM = 0.886\frac{\lambda}{NA^2}$$

That is, it is found that the vertical resoling power in the HOCT has a relation with it similar to that of the signal light with an extent of amplification degree (a matching degree of the wave surfaces) by the reference light, in other words, the depth of focus. Accordingly, since the more NA of the objective optical element, that is, the magnification of the lens is increased, the more the HOCT can improve not only a plane resolving power of a substance surface but also the vertical resolving power thereof simultaneously therewith, the technology is favorable for high resolving power three-dimensional observation of the observation substance.

(B) Vertical Resolving Power of Conventional OCT

It is supposed that a low interference light spectrum including the SLD (super luminescent diode) takes a Gaussian-type power spectral density shown in the following formula (B-1).

$$S(\nu) = \frac{2\sqrt{\ln 2/\pi}}{\Delta\nu}\exp\left[-4\ln 2\left(\frac{\nu-\nu_0}{\Delta\nu}\right)^2\right] \quad [\text{B-1}]$$

Here, ν is a frequency of light (ν=c/λ), $\nu_0$ and Δν are a central frequency and a spectral width of incident light. c is a light speed and λ denotes a wavelength of the light. Considering interference of light expressed by the formula (B-1), intensity $I_d$ of light received by the OCT detection unit is expressed by the following formula (B-2).

$$I_d = \langle|E_d|^2\rangle = 0.5(I_r+I'_s)+Re\{\langle E_r^*(t+\tau)E'_s(t)\rangle\} \quad [\text{B-2}]$$

Here, $I_r$ and $I_s$ are intensities of reflected light from a reference light path and a measurement light path respectively, $E_r$ and $E_s$ are complex amplitudes of the reflected light therefrom respectively. A dash (') indicates that it has undergone a change by a measurement sample. ≤ and ≥ denote time averages. The interference light component $\le E_r^*(t+\tau)E_s'(t)\ge$ is defined as a mutual coherence function and has a form that an inner product of mutual complex numbers has been expressed in time average.

A mirror (reflectance=1) which is ideal as the measurement sample is supposed and an interference light component |G(ν)| when streaks of light from the light source of the Gauss spectrum expressed by the formula {B-1} have been made to interfere with each other is obtained. The interference light component |G(v)| can be obtained by extending the calculation of interference by the previous single wavelength light source. That is, it is expressed by the following formula (B-3) as the one that streaks of light which are different from one another in spectrum and intensity have been superposed countlessly.

$$G(\tau) = \int_0^\infty S(v) \exp(-j2\pi v\tau) dv \quad [\text{B-3}]$$

In the following, a solution is found by substituting the formula (B-1) for formula (B-3).

$$G(\tau) = \int_0^\infty \frac{2\sqrt{\ln 2/\pi}}{\Delta v} \exp\left[-4\ln 2\left(\frac{v-v_0}{\Delta v}\right)^2\right] \exp(-j2\pi v\tau) dv \quad [\text{B-3'}]$$

Here, the formula (B-3') is simplified by utilizing a relation between the following formulae (B-4-1) and (B-4-2).

$$\frac{2\sqrt{\ln 2/\pi}}{\Delta v}(v-v_0) = f \Rightarrow \frac{2\sqrt{\ln 2/\pi}}{\Delta v} dv = df \quad [\text{B-4-1}]$$

$$t = \frac{\Delta v}{2\sqrt{\ln 2/\pi}} \tau \quad [\text{B-4-2}]$$

The formula (B-3') is finally simplified to the following formula (B-5).

$$G(\tau) = \exp\left[-\left(\frac{\pi \Delta v \tau}{2\sqrt{\ln 2}}\right)^2\right] \exp(-j2\pi v_0 \tau) \quad [\text{B-5}]$$

$\tau$ is a time difference when the streaks of light interfere with each other and $\tau = (L_s - L_r)/c$. If it is expressed as $L_s = L_r - VT$ (V is a reference mirror moving speed, T is a time) using $L_s$ and $L_r$ as standards, it will turn into the difference which depends on the speed as expressed by the following formula (B-6).

$$\tau = \frac{V}{c} T \quad [\text{B-6}]$$

The formula (B-5) indicates that the light source having a Gaussian type spectral distribution has a spindle-shaped interference waveform (an interferogram) and the intensity thereof undergoes exponential attenuation depending on the speed. The Gaussian type power spectral distribution also applies to an LED, a laser and so forth regardless of the low coherence light source. That is, the intensity of the interference light will attenuate depending on the speed unless it is the ideal single wavelength light source.

The interferogram shows the coherence of the light source and its interference distance (a coherence distance) depends on the spectral width of the light source. The spectral width of the light source can be interpreted as an amount which directly depends on a time $\Delta t$ that the light emitted from the ideal single wavelength light source maintains its constant frequency and it satisfies a relation in the following formula (B-7).

$$\Delta t \cdot \Delta \tau \approx 1 \quad [\text{B-7}]$$

This coherence distance is expressed as a coherence length $I_c$. Visibility of the interference light is expressed as in the following formula (B-8) in the OCT.

$$\text{Visibility} = \frac{I_{max} - I_{min}}{I_{max} + I_{min}} \quad [\text{B-8}]$$

Here, the coherence length $I_c$ has been defined by an optical path difference $\Delta L$ $(=L_r-L_s)$ when the visibility of the interference light amounts to $\sqrt{1/2}$. That is, it exhibits the optical path difference when $|G(\tau)|=1/2$ in the formula (B-5) which has expressed the item of the interference light. At this time, the coherence length relative to light source wavelengths (a central wavelength $\lambda_0$ and a wavelength half width at half maximum $\Delta\lambda$) can be expressed by the following formula (B-9) by using a relation of (v=c/λ).

$$I_c = \frac{2c \cdot \ln 2}{\pi \Delta v} = \frac{2\ln 2 \lambda_0^2}{\pi \Delta \lambda} \quad [\text{B-9}]$$

Since the relation between the vertical resolving power and the coherence length substantially matches it, FWHM can be expressed by the following formula.

$$\therefore FWHM \approx I_c = 0.441 \frac{\lambda^2}{\Delta \lambda} \quad [\text{B-10}]$$

That is, it is found that in the conventional OCT, the high vertical resolving power can be realized by using the light source which is large in wavelength half value at half maximum $\Delta\lambda$. Incidentally, the visibility of the interference light which can be detected is made different depending on signal processing of the detection signal. Although, in the above formula (B-10), the visibility is supposed to be $\sqrt{1/2}$, it is desirable that the visibility be in a range of $\sqrt{1/e^2}-\sqrt{1/2}$ when the existing product is assumed. At this time, if $k_1$ is a constant corresponding to the constant 0.441 on the right side of the formula (B-10), the constant $k_1$ will be $0.441 \leq k_1 \leq 0.750$. A relation between the wavelength half width at half maximum of the light source and the vertical resolving power in the abovementioned range of $k_1$ is shown in FIG. 7. It is found also from FIG. 7 that the relation between the wavelength half width at half maximum and the resolving power of the conventional OCT well matches the above formula (B-10).

(C) Vertical Resolving Power of Confocal Microscope

A signal $I_{CON}$ obtained by the confocal microscope can be expressed by the following formula (C-1) as integral calculus of the intensity of light which is incident upon the detector because direct intensity detect on is made.

$$I_{CON} = \int_D |E_s|^2 dr \quad [\text{C-1}]$$

When a spot radius $r_{s,obj}$ on the substance surface (=the sample condensing surface) is considered geometrically, it is made into the following formula (C-2).

$$r_{s,obj} = 2z \tan(\sin^{-1} NA) \quad [\text{C-2}]$$

Further, supposing that M is a magnification of a returning-way optical system ratio in focal length of the objective optical element [the objective lens] to the detection system objective optical element [the detection system condensing lens]), a spot diameter $r_{s,det}$ will reach the M-fold size on the imaging surface, that is, on the photodetector as in the following formula (C-3), from the relation between the substance surface and the imaging surface.

$$r_{s,det} = M \cdot 2z \tan(\sin^{-1} NA) \quad [C\text{-}3]$$

Here, for simplicity, supposing that the intensity distribution of light on the photodetector is constant, the signal $I_{CON}$ which is incident upon and detected by the photodetector of an "effective area S" on the imaging surface, that is, the photodetector will be as in the following formula (C-4). Here, the "effective area S" is an area obtained after the influence of the light-shield element and so forth such as the pin hole arranged on the surface of the photodetector as used in the general confocal microscope has been included. That is, the smaller the size of the photodetector is made, the smaller S becomes. On the other hand, S becomes small also when the small pin hole is arranged on the photodetector without changing the size of the photodetector.

$$I_{CON}(z) \approx \frac{S}{\pi (M \cdot r_{s,det})^2} |E_s|^2 = |E_s|^2 \frac{1}{4\pi \tan^2(\sin^{-1} NA)} \frac{S}{M^2} \frac{1}{z^2} \quad [C\text{-}4]$$

As apparent from the formula (C-4), the signal intensity in the confocal microscope is determined depending on whether or not the light of the detected amount enters the photodetector. The FWHM in the confocal microscope can be expressed by the following formula (C-5).

$$\frac{1}{4\pi \tan^2(\sin^{-1} NA)} \frac{S}{M^2} \frac{1}{z^2} \leq \frac{1}{2} \quad [C\text{-}5]$$

$$\therefore FWHM = 0.798 \sqrt{\frac{S}{M^2}} \frac{\sqrt{1-NA^2}}{NA}$$

It is found that in the confocal microscope, the resolving power depends on the effective area $S/M^2$ and NA of the photodetector which has been standardized with the lateral magnification (the smaller the effective area S of the photodetector is and the larger NA is, the more the resolving power is increased) and does not depend on the wavelength $\lambda$.

(D) Conditions that Heightening of Resolving Power by HOCT is Realized

From the foregoing study, it is found that the HOCT can obtain the high vertical resolving power in a case of satisfying the following formulae (D-1) and (D-2).

$$0.886 \frac{\lambda}{NA^2} \leq 0.441 \frac{\lambda^2}{\Delta \lambda} \quad [D\text{-}1]$$

$$0.886 \frac{\lambda}{NA^2} \leq 0.798 \sqrt{\frac{S}{M^2}} \frac{\sqrt{1-NA^2}}{NA} \quad [D\text{-}2]$$

The constant 0.441 used in the formula (D-1) is given by the optical path difference when the visibility of the interference light amounts to $\sqrt{1/2}$ as used in the formula (B-9) and the constant varies depending on up to which % a threshold value of the visibility is allowed. Therefore, when describing again them by using the constant $k_1$ ($0.441 \leq k_1 \leq 0.750$), the following formulae (D-3) and (D-4) can be derived.

$$\frac{1}{NA^2} \leq \frac{k_1}{0.886} \frac{\lambda}{\Delta \lambda} \quad [D\text{-}3]$$
$$0.441 \leq k_1 \leq 0.750$$

$$\frac{\lambda}{(NA\sqrt{1-NA^2})} \leq 0.901 \sqrt{\frac{S}{M^2}} \quad [D\text{-}4]$$

That is, the above formula (D-3) indicates that the vertical resolving power which is better than the effect of "$\lambda/\Delta\lambda$" indicating the coherence of the light source obtained by the conventional OCT can be obtained by heightening the numerical aperture NA (the magnification of the objective lens) of the objective optical element of the HOCT.

In addition, the above formula (D-4) indicates that the vertical resolving power which is more excellent than the effect of the effective detector size "$\sqrt{S}/M^2$" which has been standardized with the lateral magnification obtained in the confocal microscope can be obtained by selecting a rising extent ($\lambda/(NA\sqrt{1-NA^2})$) of the wave surface. These conditions will be described in detail in the following specific configurations of the present invention.

Incidentally, if ranges indicated by the following formula (D-5) are selected by way of example, the above formulae (D-3) and (D-4) can be satisfied.

$400 \leq \lambda \leq 850$ (nm)

$0 \leq \Delta\lambda \leq 25$ (nm)

$0.25 \leq NA \leq 0.9$ $4 \leq S \leq 100$ (μm²)

$2 \leq M \leq 10$ (however, $2 \leq \sqrt{(S/M^2)} \leq 10$ (μm)). [D-5]

(E) Configuration of Full-Fielded HOCT

The full-field OCT is known as the OCT which can realize high-speed measurement. in the conventional OCT, when performing plane image acquisition, the laser light has been scanned over the sample surface, while, in the full-field OCT, the reference light is used similarly to the OCT and then the entire surface of the visual field of the observation surface on which the sample has been placed is projected again onto an area detector by using illumination light as the signal light similarly to the general optical microscope, and in-plane signals are acquired in bulk by making the signal light interfere with the reference light on the area detector. The time required for acquiring the plane images by the general OCT was the time for scanning the laser used in measurement, that is, the time which is proportional to the resolution of the acquired image. On the other hand, in the full-field OCT, the resolution of the acquired image can be determined only by the area detector used, by preparing an appropriate optical system and a reduction in measurement time, that is, speeding-up of the OCT device becomes possible even when, in particular, a high-resolution detector has been used.

As for these full-field OCTs, there is a research paper (Optics Letters, Vol. 23, Issue 4 (1998), pp. 244-246) that bulk acquisition of xy plane images in the visual field of 500 μm has been performed by using a CCD camera as the detector and acquiring the OCT signal while applying the surface light source to the observation sample. In addition, there is also a research paper (Optics Letters, Vol. 28, No. 10 (2003), pp. 816-818) that bulk acquisition of the xy plane OCT images that the time required for tomographic image acquisition has been speeded up has been performed by using two cameras. At this time, the big difference from the conventional OCT device as the constituting component is the size of the detector.

Also in a case where the full-fielded HOCT is to be realized, the conditions required for obtaining the high vertical resolving power by the HOCT are the same as those in the above formulae (D-3) and (D-4). However, as the detector, not one photodetector (PD) but a photodetector in which a plurality of detection circuits have been two-dimensionally arranged is needed for plane bulk acquisition. As typical photodetectors, image pick-up elements such as a CCD (a charge-coupled device) image sensor, a CMOS (complementary type metal oxide film semiconductor field effect transistor) image sensor and so forth are well known. The size of one detection circuit which configures these photodetectors is several tm to several ten μm and is greatly reduced in comparison with several hundred pan of the general PD (photodiode).

Although it is possible to detect the interference signals of different phases by using the plurality of PDs in the HOCT, a method of realizing the full-field HOCT by using the plurality of CCDs or CMOSs and so forth not only has difficulty in adjusting the positions of the plurality of photodetectors but also there exist many problems therein including synchronization of signals from the plurality of photodetectors when acquiring the signals. Accordingly, the inventors of the present invention have paid attention to the point that the size of the detection circuit in the photodetector becomes small and have found out a configuration of realizing phase diversity detection by one photodetector in a state where the high resolving power is maintained.

An element for allowing only light which is different in phase to pass through, that is, a polarizer is arranged for each of the detection circuits in the immediate vicinity to the detection circuits which configure the photodetector. The polarizers so arranged are oriented in different azimuths for every adjacent detection circuits (pixels), and a region segmentation polarizer which can acquire signals required for the phase diversity detection from 2×2 pixels is provided on the photodetector. In this system, the resolution is reduced to a half (a half vertically and horizontally) in appearance. However, if the size of the 2×2 pixels is small in comparison with that of the light spot after the lateral magnification has been incorporated, the obtained image will not be greatly degraded in comparison with a high-magnification image.

The abovementioned conditions are expressed by the following formula (E-1).

$$2 \times 0.61 \frac{\lambda}{NA} \times M \leq 2 \times \sqrt{S} \qquad [\text{E-1}]$$

The left side of the above formula (E-1) is the one that the spot size calculated from the Rayleigh criterion has been multiplied by the lateral magnification, and the right side is the detector size corresponding to the 2×2 pixels.

If a relational formula is simplified by erasing the standardized lateral magnification ($\sqrt{S/M^2}$) with attention paid to the above formula (E-1) and the formula (D-4), the condition for NA which is favorable when realizing the full field HOCT can be obtained.

$$NA^2 \leq 0.33 \qquad [\text{E-2}]$$

The lower limit of NA is defined also in the formula (D-1), NA which is at least 0.3 is desirable when thinking it in terms of a wavelength range from a visible range to a near infrared range, and therefore the following formula (E-3) is obtained. Details of the lower limit of NA will be described in detail in the embodiments.

$$0.250 \leq NA \leq 0.574 \qquad [\text{E-3}]$$

The full field HOCT of the configuration which satisfies the formula (E-3) in addition to the above formulae (D-3) and (D-4) can realize the vertical resolving power which is high even in comparison with that of the confocal microscope.

(F) Specific Configurations of the Invention

In the present invention, the following means have been used in order to attain the abovementioned first object.

A light beam emitted from a light source is split into first and second light beams, the first light beam is condensed on a sample by an objective optical element and irradiates it therewith, the signal light reflected from the sample is guided to a plurality of detectors, the second light beam is guided to the plurality of detectors as the reference light without irradiating the sample therewith, and the signal light and the reference light are made to optically interfere with each other in a state where optical phase relations of the both are mutually different on the plurality of detectors. Thereafter, an arithmetic operation of making outputs from the plurality of detectors into inputs is performed and a result of the arithmetic operation is acquired as a detection signal which has reflected an in-sample structure at a condensing point of the first light beam. Further, the detection signals are acquired while changing the position where the first light beam is to be condensed onto the sample and thereby tomographic observation of the sample becomes possible. In such an optical tomographic observation device, when λ is the wavelength of a light source unit, Δλ is the wavelength half width at half maximum, NA is the numerical aperture of the objective optical element, S is the effective area of the detector, and M is the detection magnification of a detection surface relative to a condensing surface, there can be provided the optical tomographic observation device which has the high vertical resolving power by satisfying e relational formula of the formulae (D-3) and (D-4).

Further, as a specific configuration, each configurational parameter was set to satisfy the formula (D-5). The HOCT which satisfies this condition has the vertical resolving power which is high even in comparison with those of the conventional OCT and the confocal microscope.

Further, the detection signal which does not depend on the interference state can be obtained by performing adjustment of the arithmetic operation even in a situation that the optical system is incomplete or unstable. Specifically, in a case where the detectors which acquire the interference signals are four, the phase relation between the reference light and the signal light is set such that they are mutually different by 180 degrees on the first detector and on the second detector, are mutually different by 180 degrees on the third detector and on the fourth detector, and are mutually different by 90 degrees on the first detector and on the third detector. Thereby, four phase states that are mutually shifted by every 90 degrees in the phase relation of 360 degrees can be detected simultaneously. Since the detection signal is changed to a sinusoidal-shape one in accordance with a change of 360 degrees in phase state of light, it becomes possible to reproduce a signal state in an optional phase state by the arithmetic operation, by observing four signals which are mutually shifted in phase state by every 90 degrees. That is, stable detection in the optional phase state can be realized. As the aforementioned arithmetic operation, the sum of squares of a differential signal between the first detector and the second detector and a differential signal between the third detector and the fourth detector was given. At this time, even in a case where the optical system and so forth for acquiring the four interference signals shift from an ideal state, a constant output signal which does not depend on an interference phase can be obtained by the abovementioned arithmetic operation which is called phase diversity detection.

Further, as the light source, a point light source such as a gas laser, a solid-state laser, a semiconductor laser and an SLD that the wavelength half width at half maximum thereof is $0 \leq \Delta\lambda \leq 25$ (μm) can be used. Unlike the conventional OCT, since not only the semiconductor laser which is a high coherent light source, that is, a single wavelength light source can be used, but also a wavelength sweeping device or the spectroscope which becomes necessary in the Fourier domain OCT becomes unnecessary, it became possible to provide the inexpensive and miniaturized optical tomographic observation device.

In order to attain the second object, by way of example, the optical tomographic observation device is configured to have a light source unit, an optical head unit, a photo-detection unit, a control unit and a signal processing unit and the following means can be used. The light source unit emits a laser light beam. The optical head unit has a first optical element which branches the light beam from the light source unit into the first light beam and the second light beam, an objective optical element which condenses the first light beam onto the sample and receives reflected light, and a reference light beam reflection means provided in an optical path of the second light beam. The photo-detection unit has a photodetector including an aggregate of a plurality of detection elements, and an interference-light detection optical system for making the signal light and the reference light interfere with each other on the photodetector surface, in a relation that they are mutually different in phases for the plurality of detection elements. In such an optical tomographic observation device, when $\lambda$ is the wavelength of the light source unit, $\Delta\lambda$ is the wavelength half width at half maximum, NA is the numerical aperture of the objective optical element, S is the effective area of the detector and M is the detection magnification of a detection surface relative to a condensing surface, the optical tomographic observation device can be provided which can acquire plane images in bulk and has the high vertical resolving power by satisfying the relational formula of the formulae (D-3), (D-4) and (E-3).

Further, the photodetector is provided with a photo-detection unit in which at least four circuits which can detect a light amount by photo-electric conversion have been two-dimensionally arranged and a phase modulation plate on or in front of the photo-detection unit, and the at least four two-dimensional circuits which can detect the light amount by photo-electric conversion are combined together for every adjacent 2×2 circuits. This phase modulation plate has a function of modulating the phase of incident light such that a pair of streaks of interference light that the interference phases of the signal light and the reference light are mutually different by an integer multiple of almost 90 degrees as well as the interference phases of the signal light and the reference light are mutually different by almost 180 degrees for each circuit of the 2×2 circuits is incident upon every adjacent 2×2 detection circuits. If (M×N) is circuits which configure the photo-detection unit and $D_{(x,y)}$ is a signal acquired by each circuit, the photodetector can realize the detection system required for phase diversity detection by one detection unit by satisfying the formula (9) to be described later. This makes complicated adjustment of the plurality of detectors unnecessary and makes realization of miniaturization of the device possible simultaneously. Further, since in that detector, four pieces of phase information can be obtained simultaneously, speeding-up of the phase diversity arithmetic operation becomes possible by differentially detecting the pair of streaks of interference light that the phases are mutually different by every almost 180 degrees as in equation (10) to be described later for every pair of the 2×2 circuits.

The control unit controls the positions of the optical head and the objective lens, and a light emitting state of the semiconductor laser. The signal processing unit performs phase diversity signal processing and displays a result of a tomographic distribution of a test object on a display unit. Thereby, since the reference light and the signal light which has struck the sample and has been reflected therefrom can be detected by the two-dimensional photodetectors by synthesizing and amplifying them by the interference effect, minute reflected signals can be detected in bulk in a high S/N. That is, high-speed optical tomographic observation of the HOCT becomes possible.

The light source unit which is favorable for the optical tomographic observation device of the present invention can use not only the point light source such as the gas laser, the solid-state laser, the semiconductor laser and the SLD of which the wavelength half width at half maximum thereof is $0 \leq \Delta\lambda \leq 25$ (nm) but also a surface light source such as a light emitting diode, a surface emission semiconductor laser, an electroluminescence element of which the wavelength half width at half maximum thereof is $0 \leq \Delta\lambda < 25$ (nm).

Since, in the full-field HOCT, surface illumination becomes necessary at the condensing point, it is dealt with by using a light source enlargement unit in each of the point light source and the surface light source. For the point light source, the light source enlargement unit which has been configured by an optical waveguide and a collimate lens can be used. Owing to this configuration, a light spot on an optical waveguide outgoing end surface can be enlargedly projected onto the condensing surface of the observation sample in accordance with the lateral magnifications of the collimate lens and the objective lens. On the other hand, for the surface light source, the light spot on a light source outgoing end surface can be enlargedly projected onto the condensing surface of the observation sample in the vicinity of the condensing point by a beam expander which is configured by a plurality of lenses. By either method, it becomes possible to irradiate the observation object with the signal light which is uniform in intensity distribution.

Advantageous Effect of the Invention

According to the present invention, the interference type optical tomographic observation device which can realize the high vertical resolving power by a technique which is different from those of the OCT and the confocal microscope can be provided. Further, the interference type optical tomographic observation device by a plane bulk acquisition system which can realize the high vertical resolving power can be provided.

Subject matters, configurations and advantages effects other than the abovementioned ones will be apparent from the following description of the embodiments.

BRIEF DESCRIPTION OF DRAWINGS

FIG. 19 is a comparative table of various beam expanders.

DESCRIPTION OF EMBODIMENTS

In the following, embodiments of the present invention will be described with reference to the drawings.

First Embodiment

Figure 1:
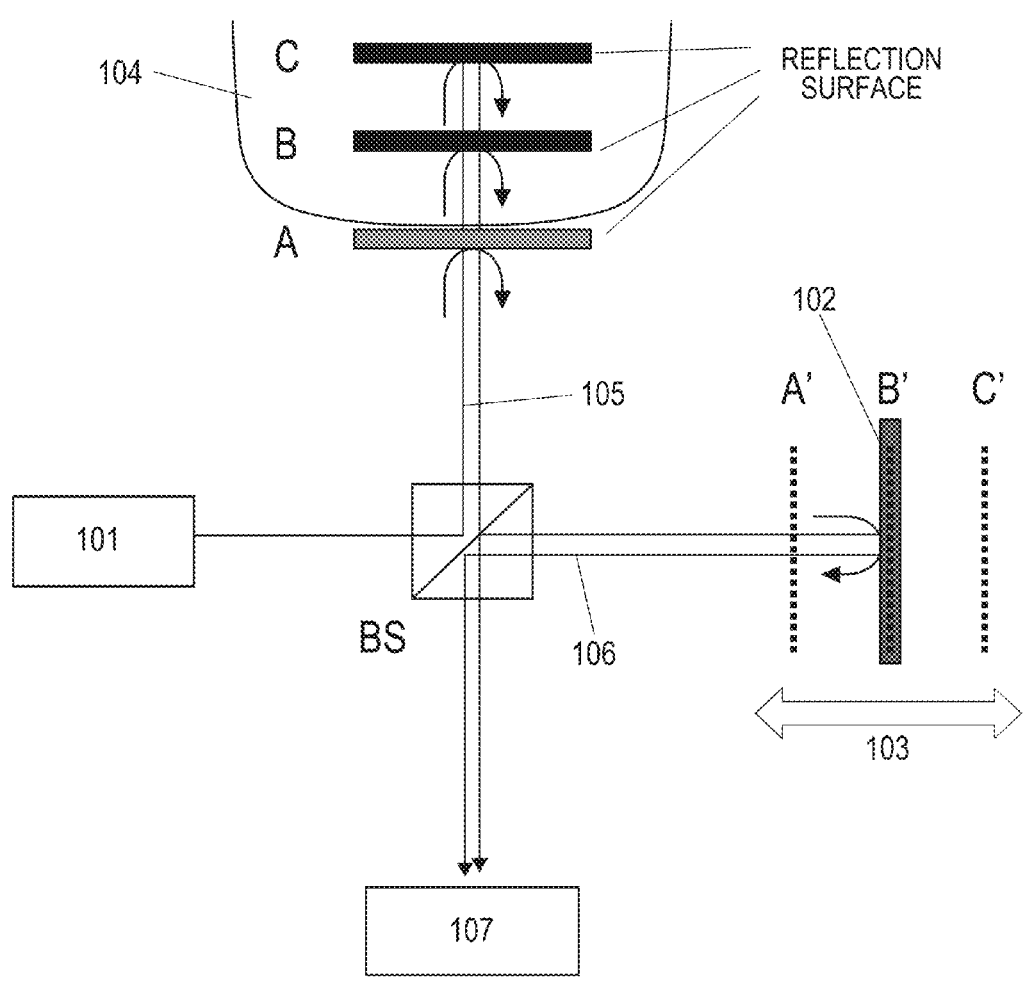
FIG. 1 is a schematic diagram showing a configuration of a conventional OCT device.
Figure 2:
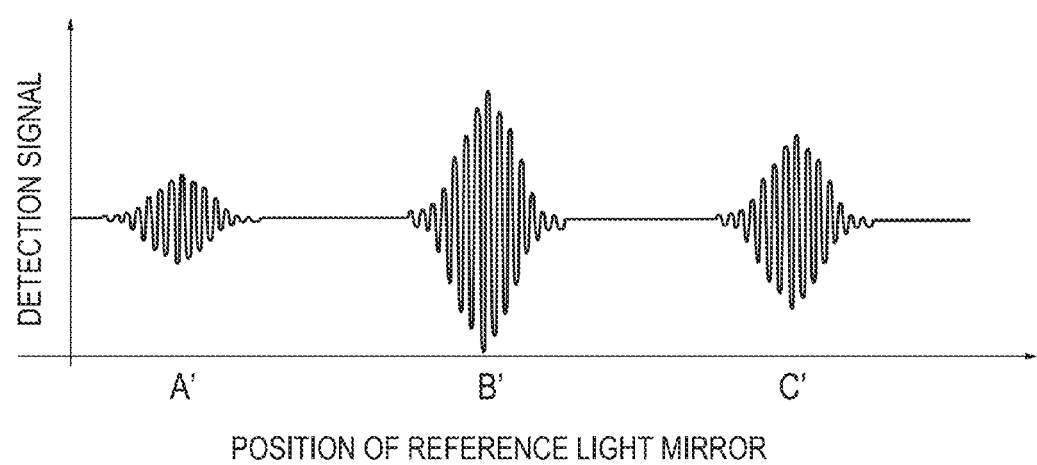
FIG. 2 is a schematic diagram of an interference signal detected by the conventional OCT device.
Figure 3:
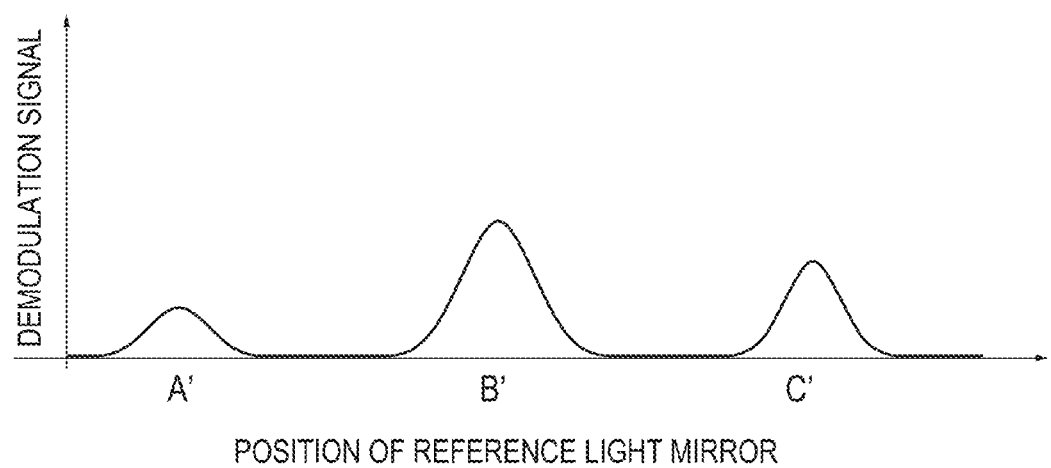
FIG. 3 is a diagram showing a demodulation signal in the conventional OCT device.
Figure 4:
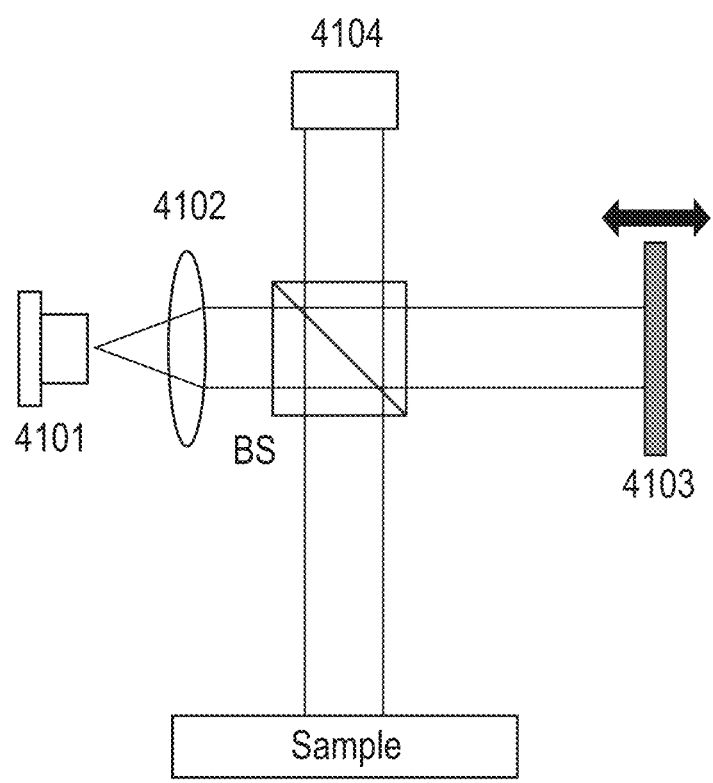
FIG. 4 is a schematic diagram showing a configuration of the conventional OCT device.
Figure 5:
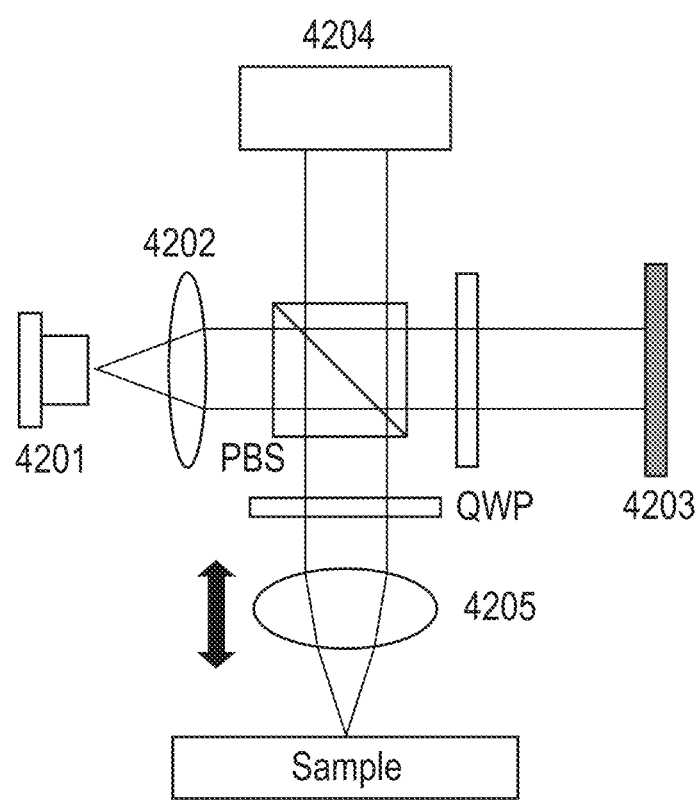
FIG. 5 is a schematic diagram showing a configurational example of a HOCT device of the present invention.
Figure 6:
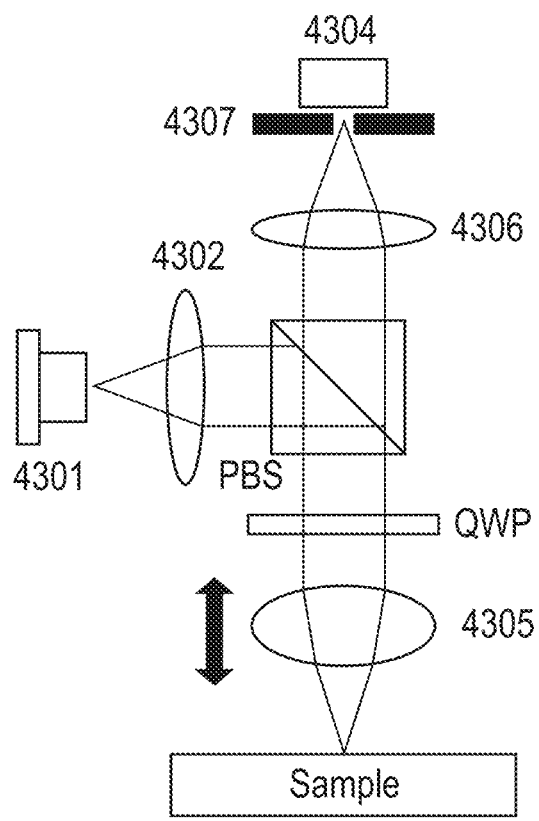
FIG. 6 is a schematic diagram showing a confocal microscope device.
Figure 7:
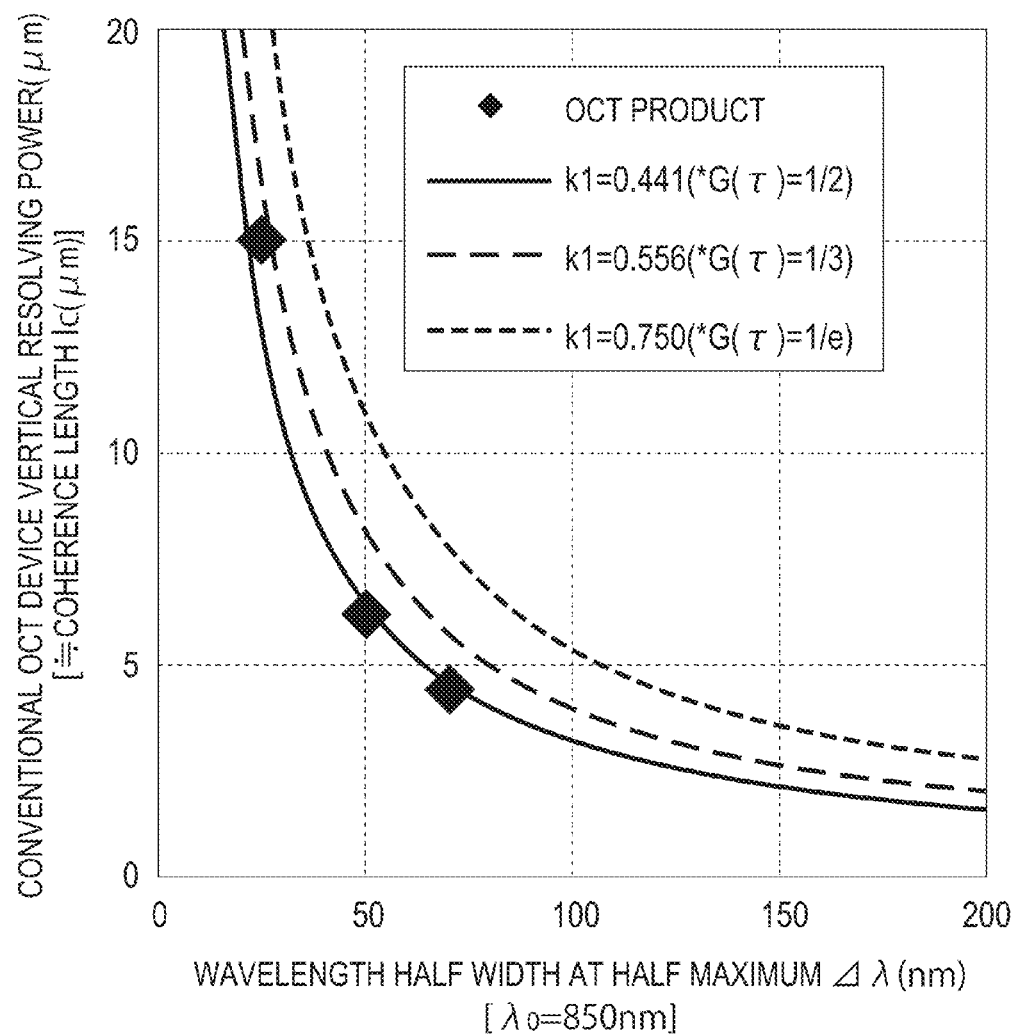
FIG. 7 is a diagram showing a relation between a wavelength half width at half maximum and a vertical resolving power in the conventional OCT.
Figure 8:
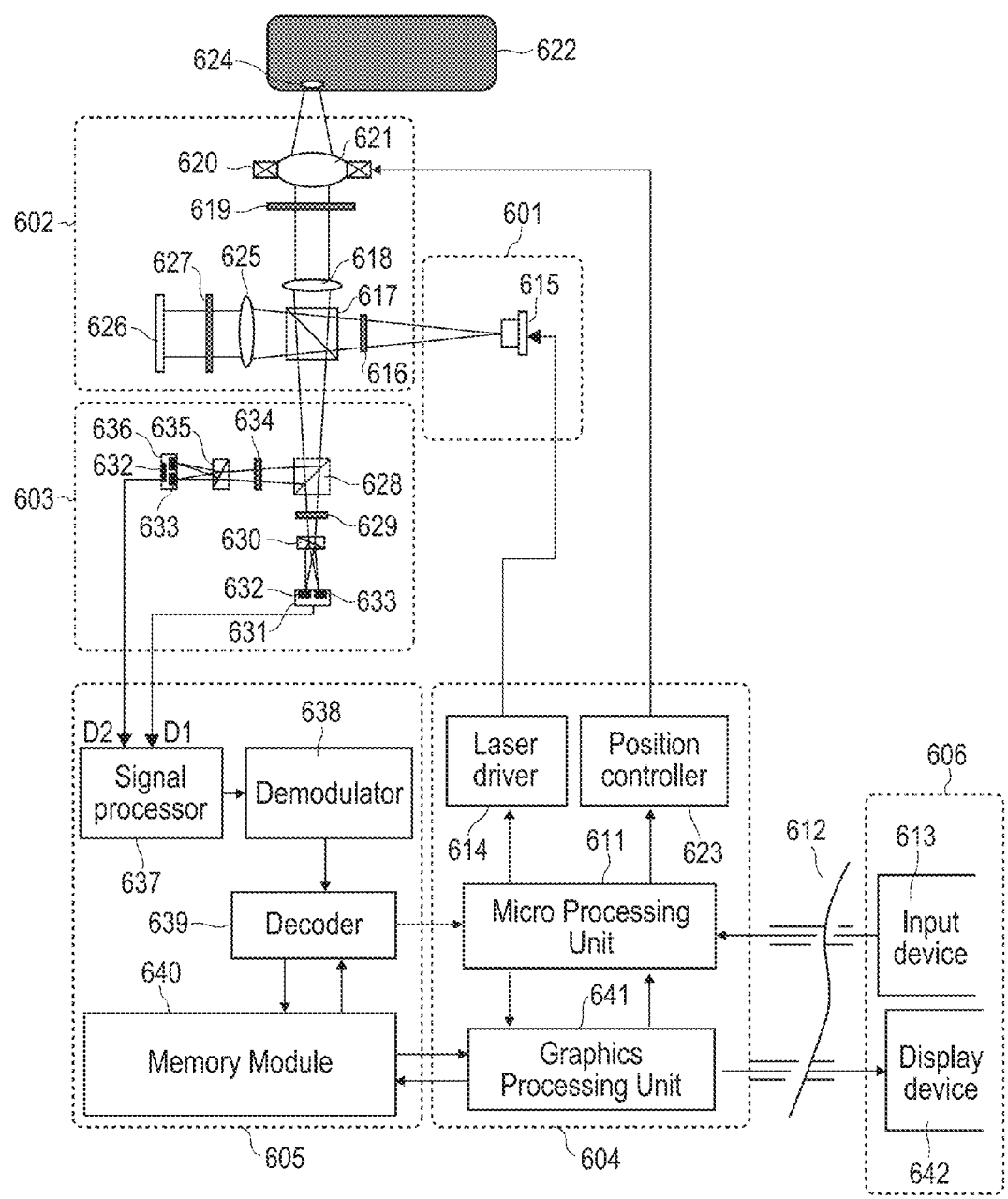
FIG. 8 is a block diagram of a HOCT device of first and second embodiments.

FIG. 8 is a block diagram of an optical tomographic observation (HOCT) device of the present embodiment. The optical tomographic observation device is provided with a light source unit 601, an optical observation head unit 602, a photo-detection unit 603, a control unit 604, a signal processing unit 605, and an information input/output unit 606.

First, operations for observing an optical tomographic structure by the present device will be described. A microprocessor 611 which is included in the control unit 604 prepares a modulation signal for measurement corresponding to optical tomographic observation conditions sent from an input device 613 included in the information input/output unit 606 which has been connected thereto via a control signal cable 612 and transmits the modulation signal to a laser driver 614.

The light source unit 601 has a light source 615. The light source 615 is driven with the modulation signal output from the laser driver 614. In the present embodiment, a semiconductor laser of 780 nm in wavelength was used as the light source.

A light beam which has been emitted from the light source 615 is guided to the optical observation head unit 602. Then, the light beam which has been guided to the optical observation head unit 602 transmits through a λ/2 plate 616. Here, an optical axis direction of the λ/2 plate 616 is set to 22.5 degrees relative to a horizontal direction and a polarization direction of the light beam is rotated 45 degrees. A polarization beam splitter 617 has a property of reflecting vertically polarized light and making horizontally polarized light transmit (all of the polarization beam splitters which will be described in the following have the same property). The light which has been rotated in polarization is split into the light beam of the vertically polarized light which is reflected by the polarization beam splitter 617 and the light beam of the horizontally polarized light which is transmitted through the polarization beam splitter 617. Of them, the reflected light beam is made into collimated light by a first collimate lens 618, thereafter passes through a λ/4 plate (an axis direction: 45 degrees relative to a horizontal polarization direction) 619 and is condensed in a sample 622 by an objective lens 621 loaded on an actuator 620. Here, a light spot 624 is scanned in the optical axis direction (an optical tomographic direction) using a control signal from a position controller 623 through the objective lens 621 loaded on the actuator 620 and thereby reflected light corresponding to an optical tomographic depth is obtained from the sample 622. In the present embodiment, an aspherical plastic lens of NA=0.55 was used for the objective lens 621.

The reflected light (hereinafter, referred to as signal light) from the sample 622 traces an optical path which is reverse to that at irradiation and is incident upon the polarization beam splitter 617 in a horizontally polarized state. On the other hand, the light beam (hereinafter, referred to as reference light) which has been transmitted through the polarization beam splitter 617 is made into a collimated light beam by a collimate lens 625, thereafter is reflected just in the opposite direction by a mirror 626, is made into vertically polarized light by reciprocally passing through a λ/4 plate 627 (the axis direction: 45 degrees relative to the horizontal polarization direction) and is again incident upon the polarization beam splitter 617. Here, the signal light and the reference light are multiplexed in a state of being mutually orthogonal in polarization and it is guided to the photo-detection unit 603.

The multiplexed light beam guided to the photo-detection unit 603 is half-divided into transmitted light and reflected light by a non-polarizing half-beam splitter 628. The transmitted light passes through a λ/2 plate 629 the optical axis of which has been set to 22.5 degrees relative to the horizontal direction to be rotated 45 degrees in polarization and is separated into a p-polarized light component and an s-polarized light component by a Wollaston prism 630. The separated light beams are respectively incident upon photodiodes 632 and 633 of a differential detector 631 and an electric signal which is proportional to a difference in intensity thereof is output from the differential detector 631. Likewise, the light beam reflected by the non-polarizing half-beam splitter 628 passes through a λ/4 plate 634 the optical axis of which has been set to 45 degrees relative to the horizontal direction and thereafter is separated by a Wollaston prism 635, and they are detected by a differential detector 636. As described later, both of the light beams which have been separated by the Wollaston prisms 630 and 635 are interference light in which the signal light interferes with the reference light, and outputs from the differential detectors 631 and 636 are the ones from which interference components have been extracted.

The outputs from the differential detectors 631 and 636 are sent to the signal processing unit 605. An output signal is sent to a digital signal processing circuit 637 provided in the signal processing unit 605, and a detection signal as light intensity of the reflected light which has reflected the optical tomographic structure can be acquired here. The obtained detection signal is demodulated by a demodulation circuit 638, thereafter is sent to a decoding circuit 639, and is stored in a memory unit 640. The detection signal stored in the memory unit 640 is sent to a display device 642 provided in the information input/output unit 606 by a graphic processor 641 provided in the control unit 604, and an operator can confirm an optical tomographic observation image at a designated position.

Here, a principle that the interference light is generated by the abovementioned operations and thereby the detection signal derived from the optical tomographic structure is obtained on the principle which is different from that of the OCT will be described. Since the light beam which is incident upon the non-polarizing half-beam splitter 628 includes the signal light as the s-polarized light component and the reference signal as the p-polarized light component, this polarization state is as follows when expressed by a Jones vector.

$$\begin{pmatrix} E_r \\ E_s \end{pmatrix}$$ [Formula 1]

Here, $E_s$ is an electric field of the signal light and $E_r$ is an electric field of the reference light. In addition, a first component of this vector indicates the p-polarized light and a second component indicates the s-polarized light. The Jones vector after this light beam has been transmitted through the non-polarizing half-beam splitter 628 and passed through the λ/2 plate 629 is as in the following formula.

$$\begin{pmatrix} \cos 45° & -\sin 45° \\ \sin 45° & \cos 45° \end{pmatrix} \begin{pmatrix} E_r/\sqrt{2} \\ E_s/\sqrt{2} \end{pmatrix} = \begin{pmatrix} (E_r - E_s)/2 \\ (E_r + E_s)/2 \end{pmatrix}$$ [Formula 2]

Next, since it is separated into the p-polarized light component and the s-polarized light component by the Wollaston prism 630, the electric fields of the separated light beams are as in the following formulae respectively, and they are made into superposition of the signal light and the reference light, that is, interference light.

½($E_r - E_s$)

½($E_r + E_s$) [Formula 3]

On the other hand, the Jones vector after the light reflected from the non-polarizing half-beam splitter 628 has passed through the λ/4 plate 634 is as follows.

$$\frac{1}{\sqrt{2}} \begin{pmatrix} i - \cos 90° & \sin 90° \\ \sin 90° & i + \cos 90° \end{pmatrix} \begin{pmatrix} E_r/\sqrt{2} \\ -E_s/\sqrt{2} \end{pmatrix} =$$ [Formula 4]

$$\begin{pmatrix} i(E_r + iE_s)/2 \\ (E_r - iE_s)/2 \end{pmatrix}$$

Next, since it is separated into the p-polarized light component and the s-polarized light component by the Wollaston prism 635, the electric fields of the separated light beams are as in the following formulae and they are made into the superposition of the signal light and the reference light, that is, the interference light as well.

$$\frac{1}{2}(E_r + iE_s)$$ [Formula 5]

$$\frac{1}{2}(E_r - iE_s)$$

Accordingly, the intensities of four streaks of interference light are as follows, a first item and a second item respectively indicate intensity components of the signal light and the reference light and a third item is an item which indicates the interference of the signal light and the reference light.

$$\left|\frac{1}{2}(E_r - E_s)\right|^2 = \frac{1}{4}|E_r|^2 + \frac{1}{4}|E_s|^2 - \frac{1}{2}|E_r E_s|\cos\Delta\phi$$ [Formula 6]

$$\left|\frac{1}{2}(E_r + E_s)\right|^2 = \frac{1}{4}|E_r|^2 + \frac{1}{4}|E_s|^2 + \frac{1}{2}|E_r E_s|\cos\Delta\phi$$

$$\left|\frac{1}{2}(E_r + iE_s)\right|^2 = \frac{1}{4}|E_r|^2 + \frac{1}{4}|E_s|^2 + \frac{1}{2}|E_r E_s|\sin\Delta\phi$$

$$\left|\frac{1}{2}(E_r - iE_s)\right|^2 = \frac{1}{4}|E_r|^2 + \frac{1}{4}|E_s|^2 - \frac{1}{2}|E_r E_s|\sin\Delta\phi$$

In the above formula, $\Delta\phi$ is a phase of the signal light with a phase of the reference light being set as a standard and this is the modulation signal to be detected. Since outputs from the differential detectors 631 and 636 are proportional to a difference in intensity between these streaks of branched light, they are made as outputs which are respectively expressed by the following formulae and are proportional to the above items indicating the interference.

$$D_1 = |E_r E_s| \cos \Delta\phi$$

$$D_2 = |E_r E_s| \sin \Delta\phi$$ [Formula 7]

The outputs from the abovementioned differential detectors 631, 636 are first A/D converted by the digital signal processing circuit 637 and thereafter are input into an arithmetic operation circuit, and the following result of arithmetic operation is output.

$$\sqrt{D_1^2 + D_2^2} = |E_r E_s|$$ [Formula 8]

It is possible to obtain a signal which is proportional to the square root of an intensity value of the signal light by generating the interference light of the signal light and the reference light and detecting it as mentioned above. If the square root in the formula (8) is omitted, there will be given a signal which has been proportional to the intensity value of the signal light. The formula (8) does not include the phase item of the electric field and indicates that optical path length correction which was required in the existing optical amplification technology and is high in nanometer accuracy becomes unnecessary. That is, the simple optical interference amplification technology is realized by using the present detection method.

Then, the reason why optical tomographic observation is possible by using the present detection technology will be shown. In the present detection technique, a substance surface of the light spot 624 which has been condensed by the objective lens 621 and observation surfaces of the four photodiodes 632 and 633 are in an imaging relation. At this time, the light spot 624 is defocused at a position remote from the substance surface in the optical tomographic direction and enters a state where the phase distribution of light has been disturbed. This indicates a state where the phase relation of the signal light with the reference light has been disturbed on the photodiodes 632 and 633 serving as observation surfaces, and sufficient signal amplification cannot be realized at this time. On the other hand, since the signal light and the reference light which are in a focused state enter a state of being in phase with each other on the photodetector, signal amplification indicated in the formula (8) is realized. That is, these results indicate that signal amplification is performed only when there is a boundary between different kinds of materials on the substance surface, that is, reflectance change occurs, and on the other hand, a stray light component which is generated in the defocused state in the general optical observation technique can be cut.

In the present embodiment, a reference sample that two sheets of cover glass of 100 μm in thickness had been nipped and inserted with silicon oil was prepared in order to evaluate the vertical resolving power. In case of one sheet of cover glass that the sample has been placed in the air, a reflected light amount of about 4% is obtained from an interface of air (the refractive index: n=1) and the glass (the refractive index: n=1.51). However, in the present invention, since it aims at detection of a low reflected light amount such as that of a biological sample, a reflected light amount of about 0.1% from an interface of the silicon oil (the refractive index: n=1.41) and the glass (the refractive index: n=1.51) was evaluated. Since nothing is nipped between the two sheets of glass, a space between the sheets of glass is about several μm.

Figure 9:
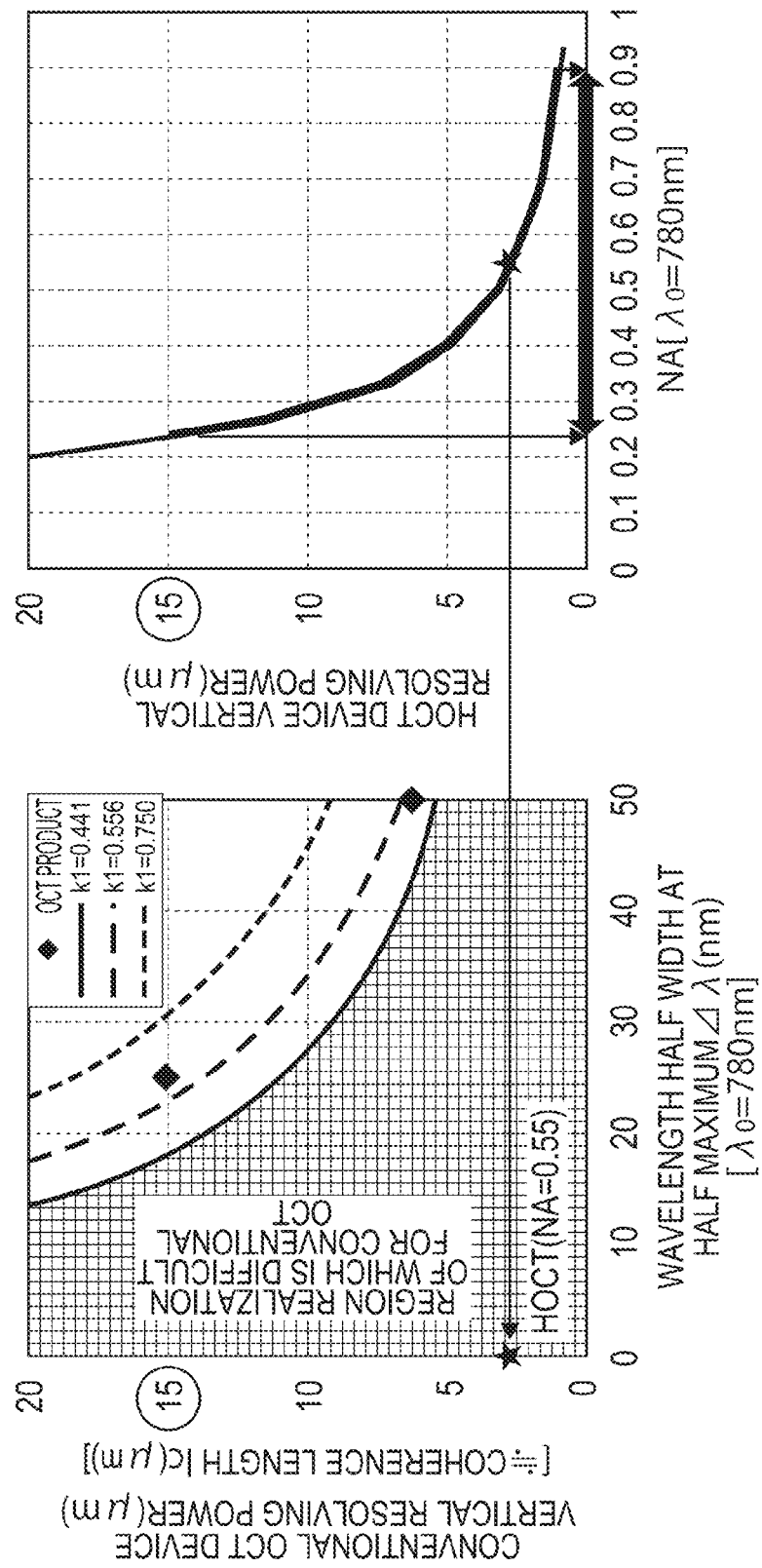
FIG. 9 are vertical resolving power comparison diagrams of the HOCT of the first embodiment and the conventional OCT.

FIG. 9 is diagrams comparatively showing the vertical resolving powers of the HOCT of the present embodiment and the conventional OCT. In addition, the mark * in the drawings shows a situation which has been realized by the present embodiment. On the left in FIG. 9, a relation between the wavelength half value at half maximum and the vertical resolving power of the light source was graphed and a region realization of which is difficult by the conventional OCT was hatched. This region is a region which satisfies the formula (D-3). On the other hand, on the right in FIG. 9, a relation between NA and the vertical resolving power in the HOCT was graphed. The right drawing in FIG. 9 shows that the vertical resolving power of the HOCT is improved with heightening NA as in the formula (A-7). Here, NA with which the HOCT vertical resolving power ≤15 μm is attained falls within a region of 0.25≤NA≤0.9 shown by an arrow on the right in FIG. 9.

Figure 10:
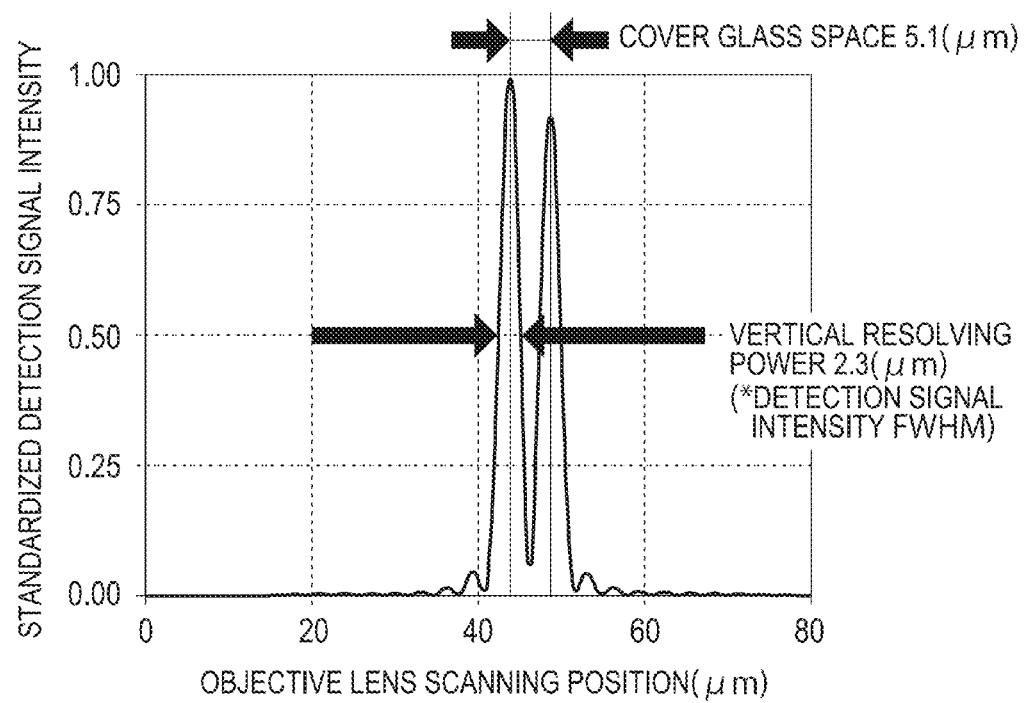
FIG. 10 is a diagram showing a detection signal for a reference sample measured by the HOCT of the first embodiment.

A result that the reference sample was measured under the condition shown by the mark * in FIG. 9 is shown in FIG. 10. As apparent from FIG. 10, it was possible to measure the cover glass space of 5 μm in the HOCT regardless of the reference sample of the low reflectance. In addition, when the vertical resolving power of the HOCT was measured with attention to a reflected signal in FIG. 10, it was confirmed that 2.3 μm could be realized.

When sorting out the above results, as shown by the mark * in FIG. 9, in the present embodiment, the vertical resolving power of 2.3 μm (the full width at half maximum FWHM of the light spot in the optical axis (z) direction) realization of which is difficult for the conventional OCT was attained by using the semiconductor laser which achieves the wavelength λ=780 nm and the wavelength half width at half maximum≤1 nm, and the objective lens of NA=0.55.

Figure 11:
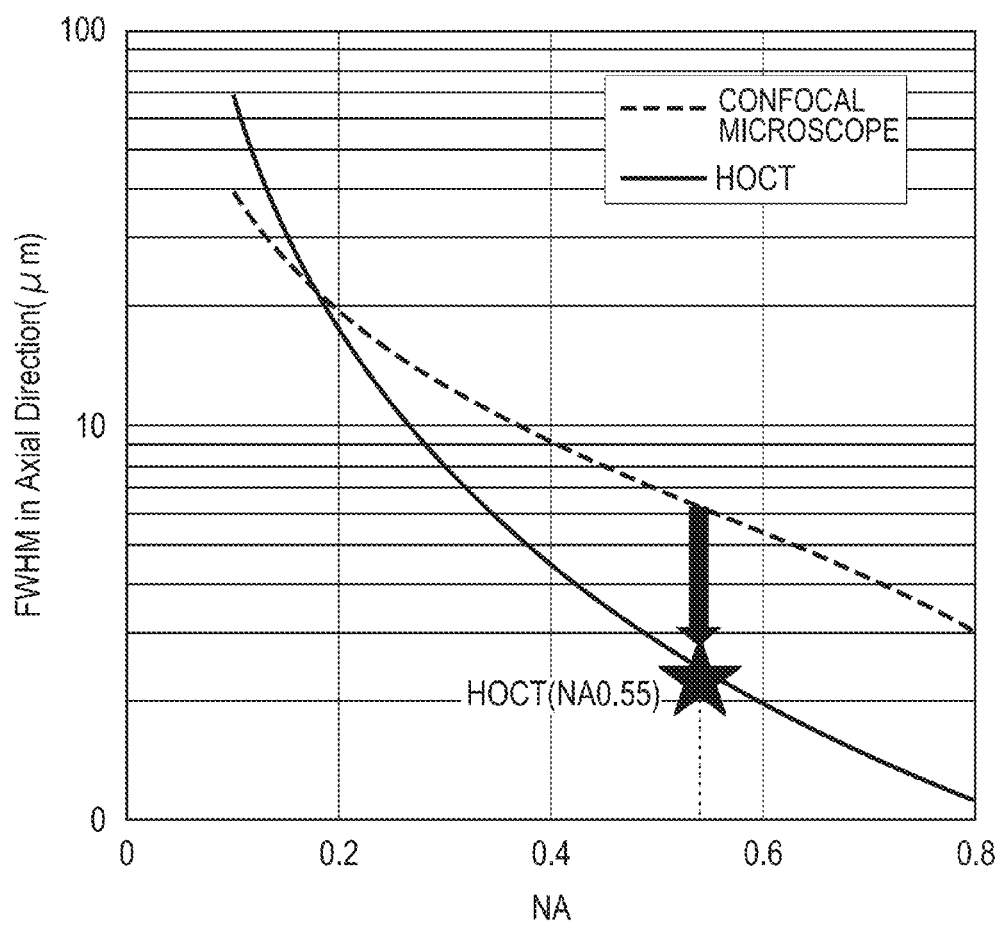
FIG. 11 is a vertical resolving power comparison diagram of the HOCT of the first embodiment and the confocal microscope.

In addition, FIG. 11 is a diagram comparatively showing the vertical resolving powers of the HOCT of the present embodiment and the confocal microscope. FIG. 11 is the one which illustrates the relations between NA and the vertical resolving power in the HOCT and the confocal microscope indicated in the above formula (A-7) and (C-5). As shown by the mark * in FIG. 11, it is found that it is difficult for the conventional confocal microscope to realize the vertical resolving power of 2.3 μm (the full width at half maximum FWHM of the light spot in the optical axis (z) direction) which has been attained by the semiconductor laser which achieves the wavelength λ=780 μm, and the objective lens of NA=0.55, the PD of the detector size S=2500 μm² (50 μm □), and the HOCT optical system of the present embodiment which achieves the detection magnification M=10.

That is, also from FIG. 9, FIG. 10, FIG. 11, it could be confirmed that in the HOCT, the vertical resolving power which exceeds that of any of the conventional OCT and the confocal microscope can be obtained by appropriately selecting NA of the objective lens, the detector size and the detection magnification even when a high coherence light source which is small in wavelength half value at half maximum was used.

In addition, in the present embodiment, the objective lens 621 is driven in the optical axis direction and in a direction orthogonal thereto by the actuator 620, aiming at miniaturization of the device and measurement time reduction. This actuator is configured by a magnetic circuit including a yoke and a permanent magnet, a movable part to which the objective lens and a drive coil have been attached, a stationary part for holding this movable part, and a support member which is connected to the stationary part and elastically supports the movable part. When a current is made to flow through the coil in a magnetic field produced by the magnetic circuit including the yoke and the permanent magnet, Lorentz force is generated and the movable part is driven in the optical axis direction or the direction orthogonal to the optical axis. That is, since it is possible to scan the objective lens by changing the current to be applied to the coil, the abovementioned actuator is favorable for acquiring an optical tomographic image by scanning the light spot.

Second Embodiment

The block diagram of an optical tomographic observation device of the present embodiment is FIG. 8 similarly to the first embodiment. In the present embodiment, not only miniaturization and simplification of the optical tomographic observation device but also heightening of the resolving power were performed, by using a semiconductor laser of the wavelength λ=405 nm for the light source 615 of the light source unit 601 and an aspherical glass lens of NA 0.85 (magnification is equivalent to ×100 times) for the objective lens 621. Other fundamental configurations and operations are the same as those in the first embodiment.

Figure 12:
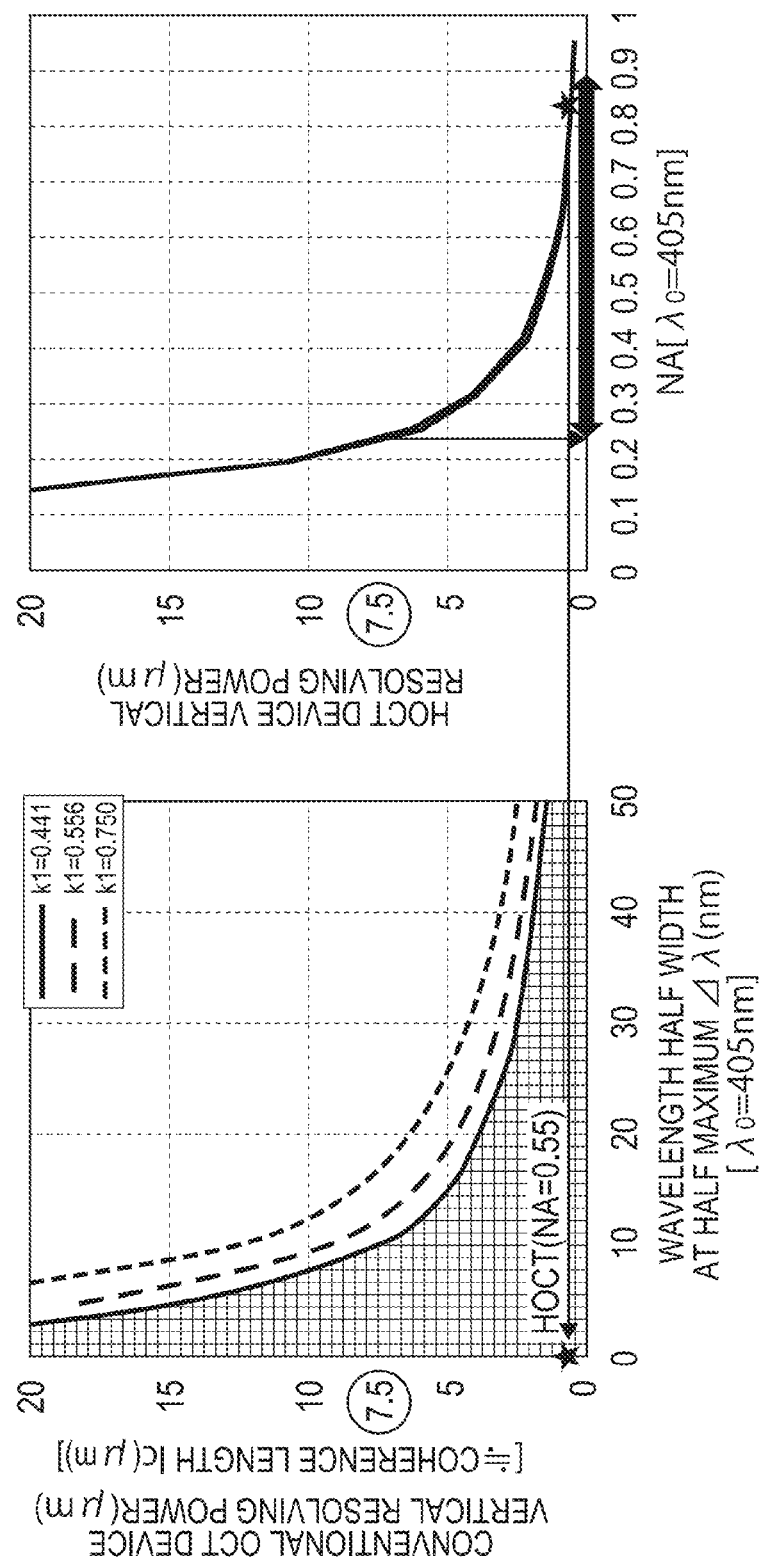
FIG. 12 are vertical resolving power comparison diagrams of the HOCT of the second embodiment and the conventional OCT.
Figure 13:
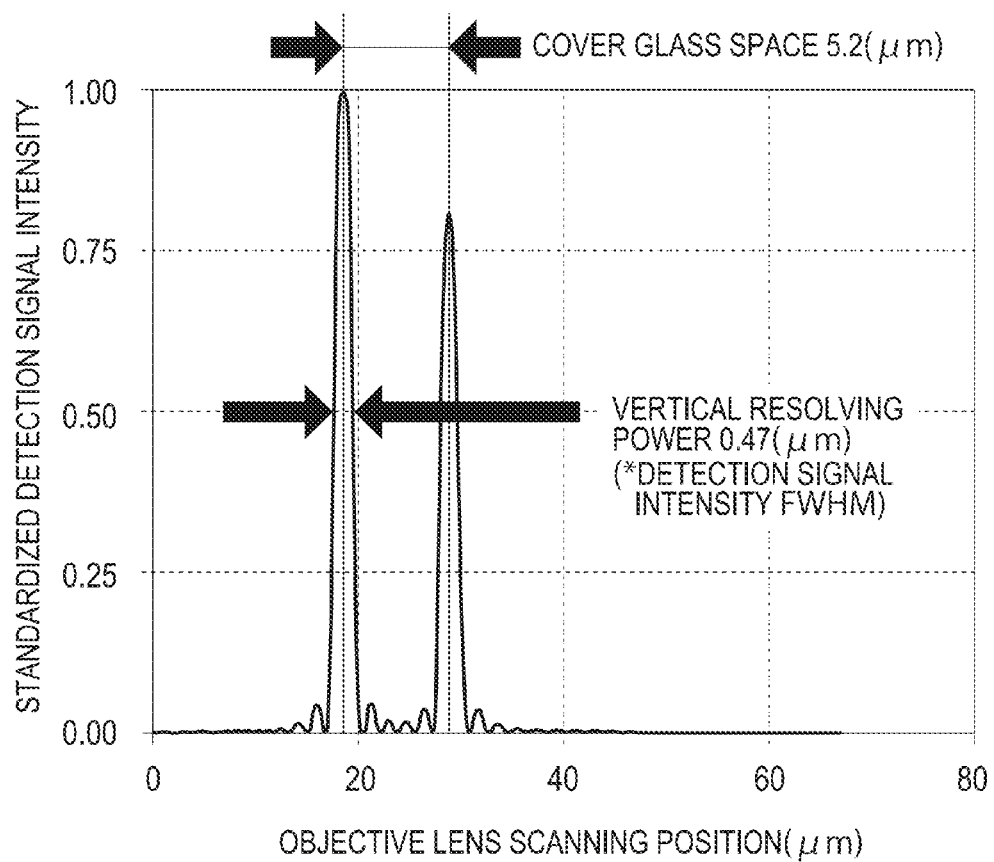
FIG. 13 is a diagram showing the detection signal for the reference sample measured by the HOCT of the second embodiment.

FIG. 12 is diagrams comparatively showing the vertical resolving powers of the HOCT of the present embodiment and the conventional OCT. The mark * in the drawings indicates the situation realized by the present embodiment. In addition, FIG. 13 is a diagram showing a result that the previously described reference sample was measured under the condition indicated by the mark * in FIG. 12. When the vertical resolving power of the HOCT was measured with attention to the detection signal in FIG. 13, it was confirmed that 0.47 μm could be realized. When sorting out the above, in the present embodiment, the vertical resolving power of 0.47 μm (the full width at half maximum FWHM of the light spot in the optical axis (z) direction) realization of which is difficult for the conventional OCT was attained by using the semiconductor laser which achieves the wavelength λ=405 nm and the wavelength half width at half maximum≤1 nm, and the objective lens of NA=0.85. It is the characteristic of the phase diversity detection that the vertical resolving power≤1 μm can be realized by using the semiconductor laser which is high in versatility in this way.

Figure 14:
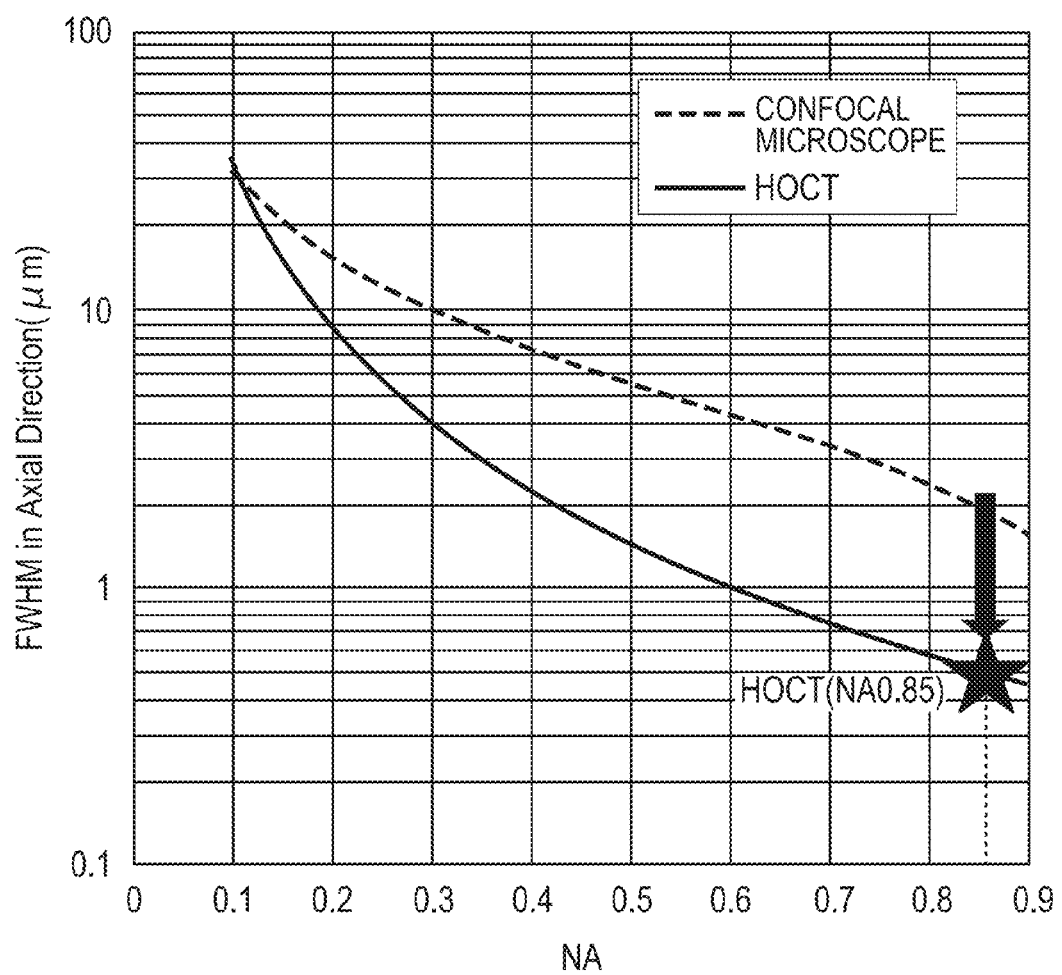
FIG. 14 is a vertical resolving power comparison diagram of the HOCT of the second embodiment and the confocal microscope.

FIG. 14 is a diagram comparatively showing the vertical resolving powers of the HOCT of the present embodiment and the confocal microscope. As shown by the mark * in FIG. 14, it is found that it is difficult for even the confocal microscope to realize the vertical resolving power of 0.47 μm (the full width at half maximum FWHM of the light spot in the optical axis (z) direction) which was attained by using the semiconductor laser of the wavelength λ=405 nm, the objective lens of NA=0.85, the PD of the detector size S=1600 μm² (40 μm □), and the HOCT optical system of the present embodiment of the detection magnification M=10.

That is, also from FIG. 12, FIG. 13, FIG. 14, it could be confirmed that in the HOCT, the vertical resolving power≤0.5 μm which not only exceeds the vertical resolving power of any of the conventional OCT and the confocal microscope but also is said to be difficult for the conventional optical measurement technology could be obtained by appropriately selecting NA of the objective lens, the detector size, and the detection magnification even when a high coherence light source which is small in wavelength half width at half maximum was used.

In the second embodiment, NA with which the HOCT vertical resolving power≤7.5 μm the superiority of which is definite in comparison with the conventional OCT is attained falls within the region of 0.25≤NA≤0.9 from FIG. 12. Since the vertical resolving power of the HOCT is proportional to the wavelength λ of the light source, it is obvious also from the above formula (A-3) that, like the wavelength has been reduced to almost half in comparison with the wavelength of the first embodiment, NA which satisfies the vertical resolving power which is half the magnitude thereof falls within the same range (0.25≤NA≤0.9) as the range of the first embodiment and the second embodiment. That is, it is found also from the first embodiment and the second embodiment that a lower limit value of NA which is required for the HOCT in order to exhibit the resolving power which is higher than the resolving power of the conventional OCT not depending on the wavelength of the light source is NA≥0.25.

When the same range of NA (0.25≤NA≤0.9), and the measured wavelength 400 nm≤λ≤850 nm, the wavelength half width at half maximum 0≤Δλ≤25 nm have been individually set in consideration of the results of the first embodiment and the second embodiment, if the detection system, the detector size S and the detection magnification M such as those shown in the following formulae are satisfied, the formulae (D-3) and (D-4) will always be established.

$$400 \leq \lambda \leq 850 \text{ (nm)}$$

$$0 \leq \Delta\lambda \leq 25 \text{ (nm)}$$

$$0.25 \leq NA \leq 0.9$$

$$4 \leq S \leq 100 \text{ (μm}^2\text{)}$$

$$2 \leq M \leq 10$$

(however, $2 \leq \sqrt{(S/M^2)} \leq 10$ (μm))

Since the configuration parameters of the individual optical systems of the HOCT system can be independently defined by the above formulae in this way, the optical tomographic observation device which makes the high vertical resolving power possible by simple component selection without checking the complicated formulae (D-3) and (D-4) can be provided.

Third Embodiment

Figure 15:
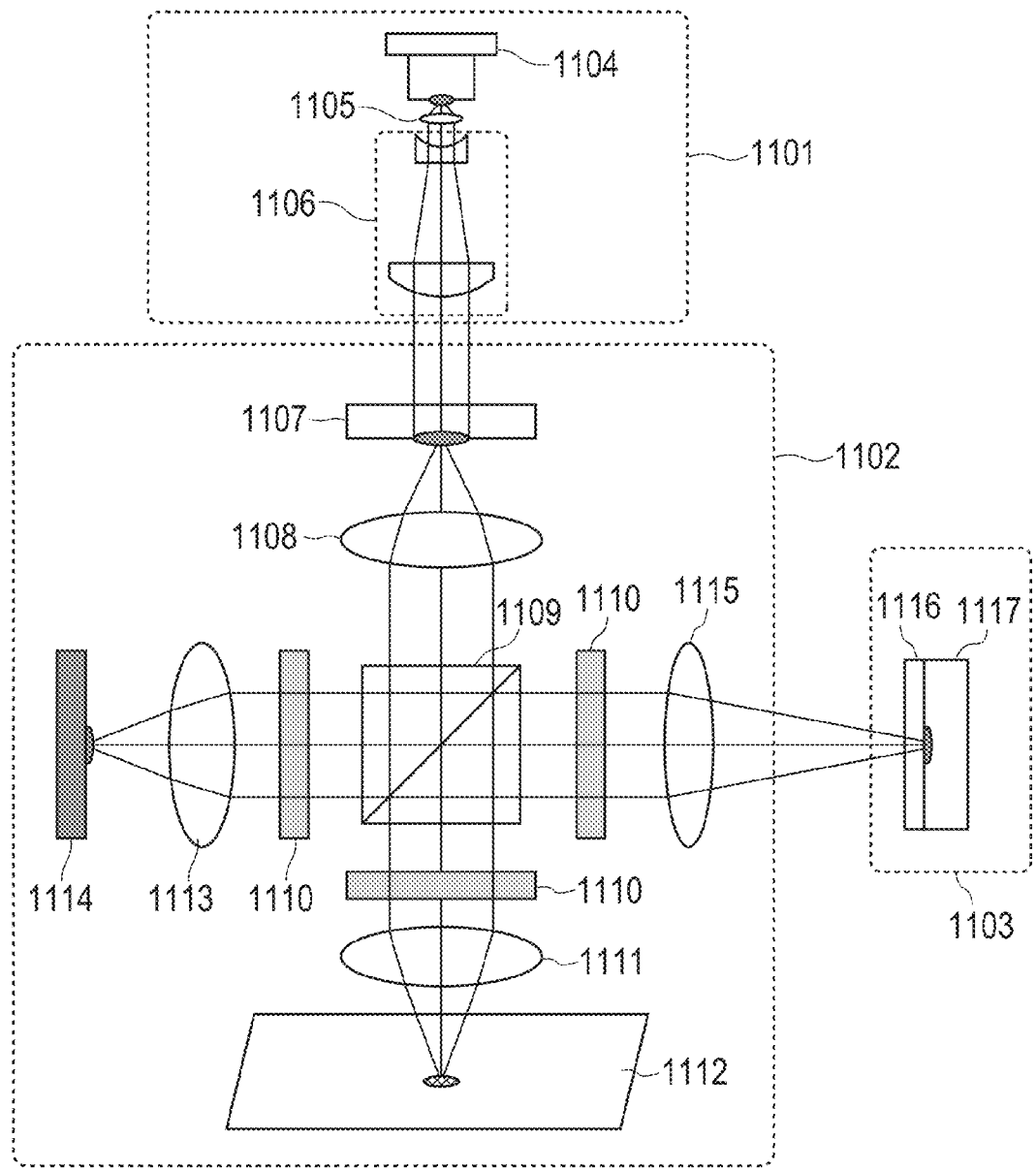
FIG. 15 is a block diagram of a HOCT device of a third embodiment.

FIG. 15 is a block diagram of an optical tomographic observation device of the present embodiment. In the present embodiment, a light source unit 1101, an optical observation head unit 1102 and a photo-detection unit 1103 were modularized, and other configurations were mad the same as those in the first and second embodiments. Further, in the present embodiment, it was configured so as to realize a full-field type one which can acquire an HOCT signal on a focal surface (an xy plane) on the observation sample, aiming at speeding-up of the HOCT. The point that the full-field type HOCT is different from the conventional OCT in configuration of the optical system lies in the configurations of the light source unit and the photo-detection unit. In the following, the configurations thereof will be described in detail. Since the configuration in the optical observation head 1102 is almost the same as those of the first and second embodiments, description using the numerical formulae and so forth is omitted.

The light source unit 1101 used in the present embodiment used a light emitting diode (LED) of the wavelength λ=520 nm and the wavelength half width at half minimum of 10 nm which is a surface light source of a spot diameter of 20 μm as a light source 1104. Since, in the full-field type one, it is necessary to perform illumination on the entirety of an observation region, the illumination size should be made the same as the size of an observation field (in the present embodiment, 200 μm). In the present embodiment, one pair of lens pairs which is called a beam expander was used in order to enlarge the spot diameter 20 μm of the LED to 200 μm on the focal surface on the observation sample.

Figure 17:
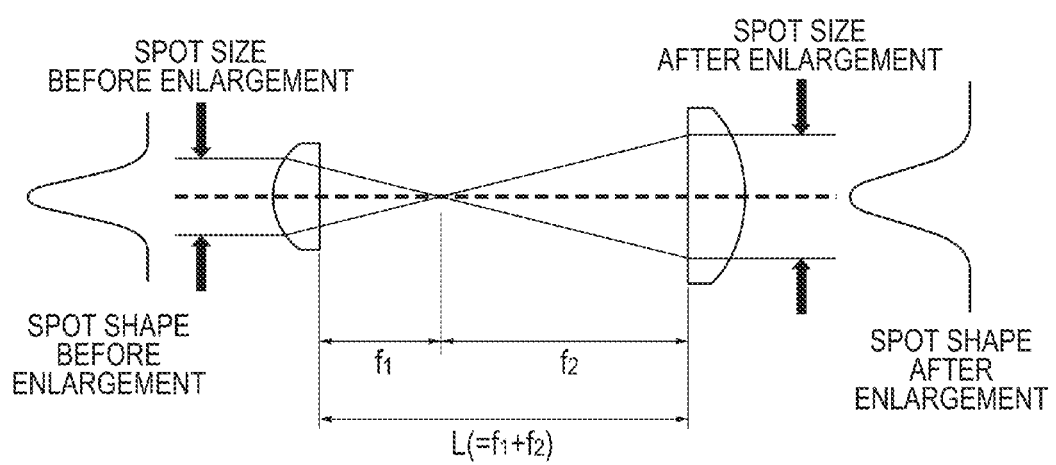
FIG. 17 is a block diagram of a Keplerian beam expander.
Figure 18:
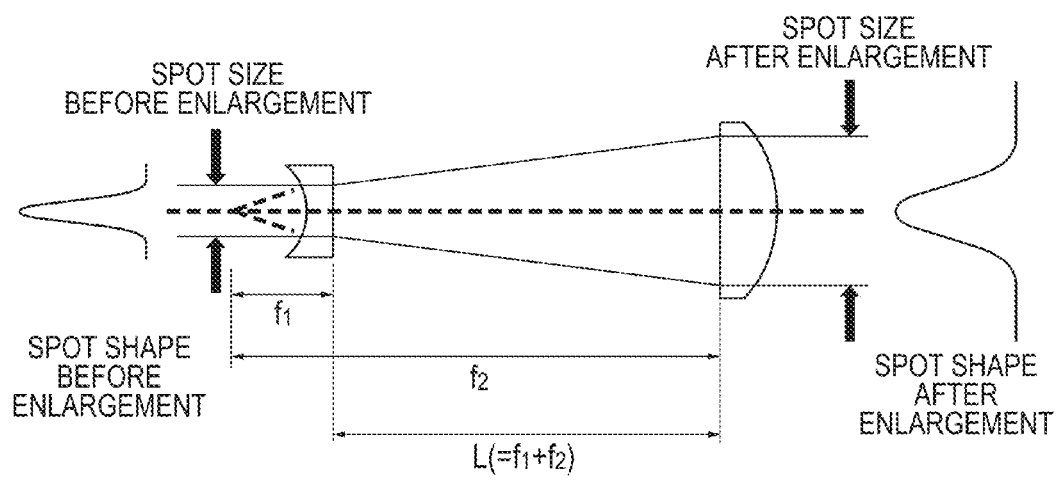
FIG. 18 is a block diagram of a Galilean beam expander.

As generally used beam expanders, a block diagram of a Keplerian beam expander is shown in FIG. 17 and a block diagram of a Galilean beam expander is shown in FIG. 18. In addition, a comparative table of various beam expanders is shown in FIG. 19. As shown in FIG. 17 to FIG. 19, it is found that the systems of the beam expanders are mutually different and the full lengths of the beam expander units are mutually different depending on a difference in kind of the lens used. In the present embodiment, in beam expander that ×10-time beam diameter enlargement is possible, the Galilean one that a beam expander full length L can be shortened to 90 mm was adopted, aiming at miniaturization of the optical system. A focal length f1 of a lens 1 used is −10 mm and a focal length f2 of a lens 2 is 100 mm.

Of course, the Keplerian one may be used and a beam expander by a combination of two or more lenses may be used unless otherwise restricted in size and so forth. The Keplerian one has an advantage that a readily available beam expander can be used, and if it is the beam expander by the combination of two or more lenses, it is also possible to structure an optical system that the magnitude of enlargement of the beam diameter can be adjusted later.

Light which has been emitted from the light source 1104 is converted into collimated light by a collimate lens 1105, the beam diameter thereof is enlarged by the aforementioned beam expander unit 1106, and the polarization direction thereof is adjusted by a λ/2 plate 1107. An objective lens 1108 is arranged so as to focus the light on a surface after it has passed through the λ/2 plate 1107. The light beam which has passed through the λ/2 plate 1107 is split into the signal light and the reference light by a polarization beam splitter 1109, the signal light is converted into circularly polarized light by a λ/4 plate 1110 and is made to irradiate a sample 1112 therewith by an objective lens 1111. A reflected signal from the sample 1112 again passes through the λ/4 plate 1110 and is guided with the photo-detection unit 1103 side in a state of having been rotated by 90 degrees in polarization via the polarization beam splitter 1109. On the other hand, the reference light was configured so as to be converted into circularly polarized light by the λ/4 plate 1110 and thereafter condensed on a mirror 1114 by a condensing lens 1113.

Here, it is preferable to select lenses of the same specification for the objective lens 1111 and the condensing lens 1113. in the present embodiment, since surface illumination is used, an off-optical axis aberration that each optical component has becomes a problem. Accordingly, if the optical systems for the signal light and the reference light are designed such that they pass through the optical components of the same kind, it will become possible to simply construct the reference optical system after these aberrations have been included.

The light reflected by the mirror 1114 again passes through the λ/4 plate 1110 and is guided with the photo-detection unit 1103 side in a state of having been rotated by 90 degrees in polarization via the polarization beam splitter 1109 similarly to the signal light. The signal light and the reference light were made to be multiplexed by the polarization beam splitter 1109, thereafter to again pass through the λ/4 plate 1110 to be converted into the circularly polarized light, and thereafter to be condensed in the photo-detection unit by a detection lens 1115. This is preparation for acquisition of four kinds of light interference signals in the later described photo-detection unit 1103 by a simple configuration. The photo-detection unit 1103 is provided with a phase modulation plate 1116 and a photodetector 1117.

In addition, in the present embodiment, lenses of the same specification were selected also for the objective lens 1108 and the objective lens 1111. The illumination size on the focal surface on the observation sample is determined by an NA ratio between these two lenses, that is, the magnification. In the present embodiment, since the lenses of the same specification were selected, the magnification herein is ×1. Therefore, the illumination size on the focal surface on the observation sample was 200 μm which is the same as the diameter of the light beam after passed through the λ/2 plate 1107.

Figure 16:
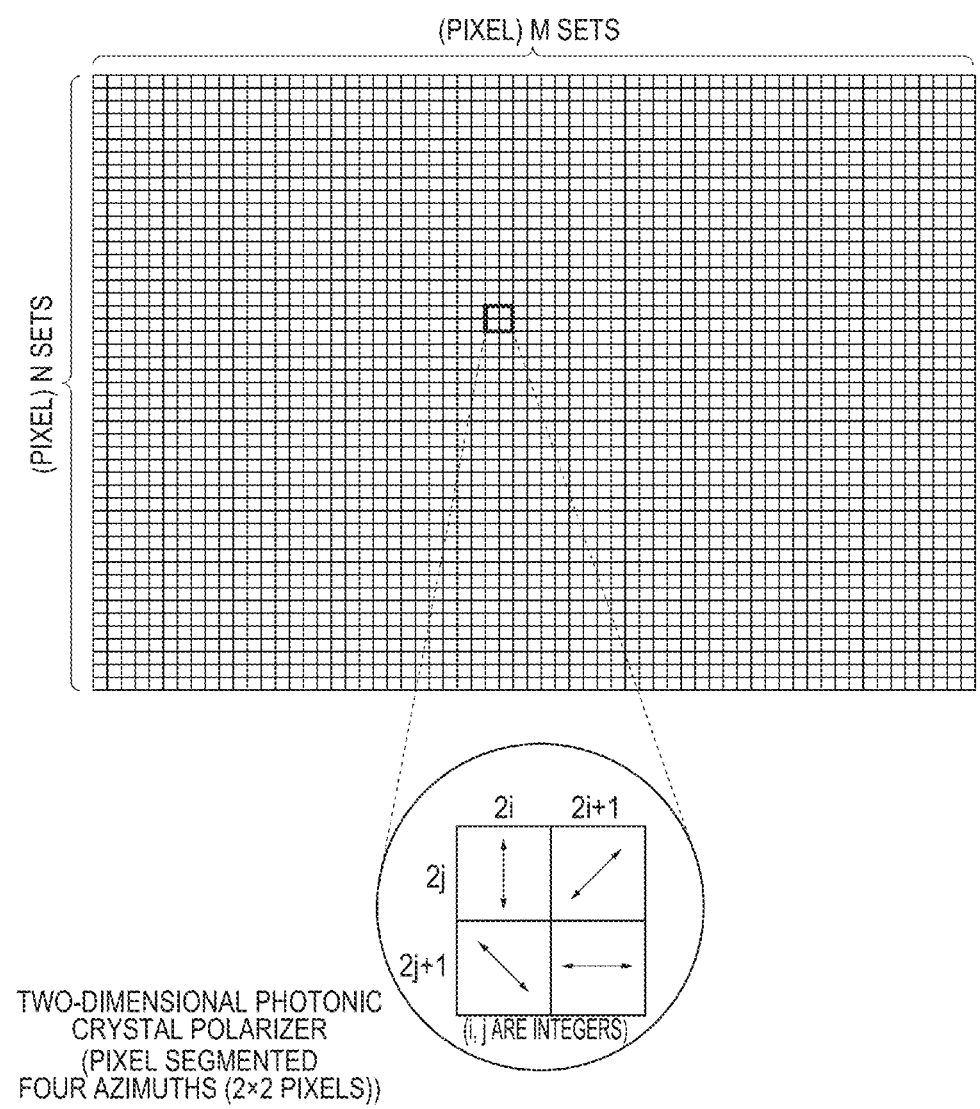
FIG. 16 is a schematic diagram of a phase modulation plate.

The phase adjustment plate 1116 used for acquiring the four kinds of the light interference signals acts as a polarizer for the light beam which has passed through it. The plurality of light interference signals required for generation of a homodyne phase diversity signal can be acquired by surface-receiving the light beams which have passed through the phase modulation plate 1116 in bulk by the photodetector 1117. A detailed function of the photo-detection unit will be described using FIG. 16. FIG. 16 is a schematic diagram of the phase modulation plate in the optical tomographic observation device of the present embodiment. The phase modulation plate is configured by a photonic crystal polarizer of a structure which is different for every region. The photonic crystal is an element which can control its optical characteristics by multiple reflection (Bragg reflection) of light which occurs in a periodic structure. Arrangement thereof on a substrate plane is, since pattern formation (lithographic drawing and so forth) is realized by a semiconductor processing technology, a multi-dimensional periodic structure of wavelength order, submicron order can be fabricated by freely setting the regions.

In the present embodiment, as the phase modulation plate, a micro-lens array element integrated with a region segmentation polarizer which has been fabricated by an auto-cloning method was adopted. The configuration is made such that the polarizers which are made mutually different in azimuth for every region are elaborated by the photonic crystals and the light beam which has passed through each polarizer is guided to each detection circuit (each pixel) provided on a CCD surface by the micro-lens array. When the phase modulation plate is combined with the CCD, different light interference signals as indicated in the following formula can be extracted by using the polarizers for four regions (directions) of 0 degree, 45 degrees, 90 degrees and 135 degrees as one unit for every CCD (2×2) pixels. In the present embodiment, not the combination of a phase plate with the polarization beam splitter but an integrated polarizing plate having different orientation axis azimuths was used. However, while the former rotates a polarization azimuth by the phase plate and segments each polarized light component by the PBS, the latter can detect only desired polarized light components on the detector by cutting the polarized light components other than those of the orientation axis azimuths by the polarizing plate, and therefore formula (9) can be obtained similarly to formula (3) and formula (5) without changing the function for performing phase modulation.

$$D_{(x,y)}=D_{(2o,2p)}=I_1=\tfrac{1}{4}|E_{sig}+E_{ref}|^2$$

$$D_{(x,y)}=D_{(2o+1,2p)}=Q_1=\tfrac{1}{4}|E_{sig}+iE_{ref}|^2$$

$$D_{(x,y)}=D_{(2o,2p+1)}=Q_2=\tfrac{1}{4}|E_{sig}-iE_{ref}|^2$$

$$D_{(x,y)}=D_{(2o+1,2p+1)}=I_2=\tfrac{1}{4}|E_{sig}-E_{ref}|^2 \quad \text{[Formula 9]}$$

However, $0<o\leq O/2$, $0<p\leq P/2$ (each of o, p, O, P is an integer), and i is an imaginary number.

Thereafter, it became possible to detect the homodyne phase diversity signal by one photodetector by performing current differentiating type differential detection on a pair of streaks of the interference light that phases are mutually different by almost every 180 degrees for every unit as indicated by the following formula.

$$\text{Sig}_{(2o,2p)}{}^2=(D_{(2o,2p)}-D_{(2o+1,2p+1)})^2+(D_{(2o+1,2p)}-D_{(2o,2p+1)})^2=(I_1-I_2)^2+(Q_1-Q_2)^2=|E_{sig}|^2|E_{ref}|^2 \quad \text{[Formula 10]}$$

Incidentally, although in the present embodiment, the photonic crystal polarizer was used for the phase modulation plate, a region-segmented polarized light filter and a diffraction grating may be used. Although it is preferable to integrate the photonic crystal polarizer with the micro-lens array and the CCD from the viewpoint of integration, it is also possible to move the phase wavelength plate to the optical observation unit side. The same advantageous effect can also be obtained by adding a pair of objective lenses to the optical observation unit side so as to form another imaging surface and inserting the abovementioned region segmented polarized light filter and diffraction grating into that imaging surface. It has such advantages that the fabrication is easy in comparison with the photonic crystal polarizer and the tolerance (the allowance) in positional adjustment of the region-segmented polarized light filter and diffraction grating can be increased by increasing the magnification on another imaging surface.

In the present embodiment, a ½-type CCD image sensor was used for the photodetector 1117. The number of CCD pixels is lengthwise×crosswise: 640×480. Of course, although a number of pixels which is larger than this may be selected, even when the signal is detected with a pixel size which is smaller than a spatial resolving power of the HOCT optical system, not only drastic image quality improvement cannot be expected but also demerits are generated from the viewpoint of a signal processing time and energy consumption. Here, it was made so as to satisfy the conditions of the formulae (D-3), (D-4) and (E-3) by setting NA of the objective lens to 0.5, the detector size S for every CCD pixel=100 μm² (10 μm □) and the detection magnification to 4. In the present embodiment, the illumination which was 200 μm on the observation surface amounts to 800 μm on the CCD detection surface and it just corresponds to the length of the diagonal of the CCD image sensor.

When $L_{FWHM}$ is an illumination size, it is preferable to satisfy the following formula.

$$L_{FWHM} \geq \{\sqrt{S} \times \sqrt{(O^2 + P_2)}\}/M$$

M: detection magnification
S: detector area for one pixel configuring the photodetector
(O×P): number of photo-detection elements configuring the photodetector Although, this time, the CCD was adopted for the photodetector in consideration of signal quality, other solid-state image pickup elements such as a CMOS image sensor may be used for the photodetector. Not only the CMOS can be manufactured cheaply but also there are merits such as high-speed responsiveness and low voltage drive.

Figure 20:
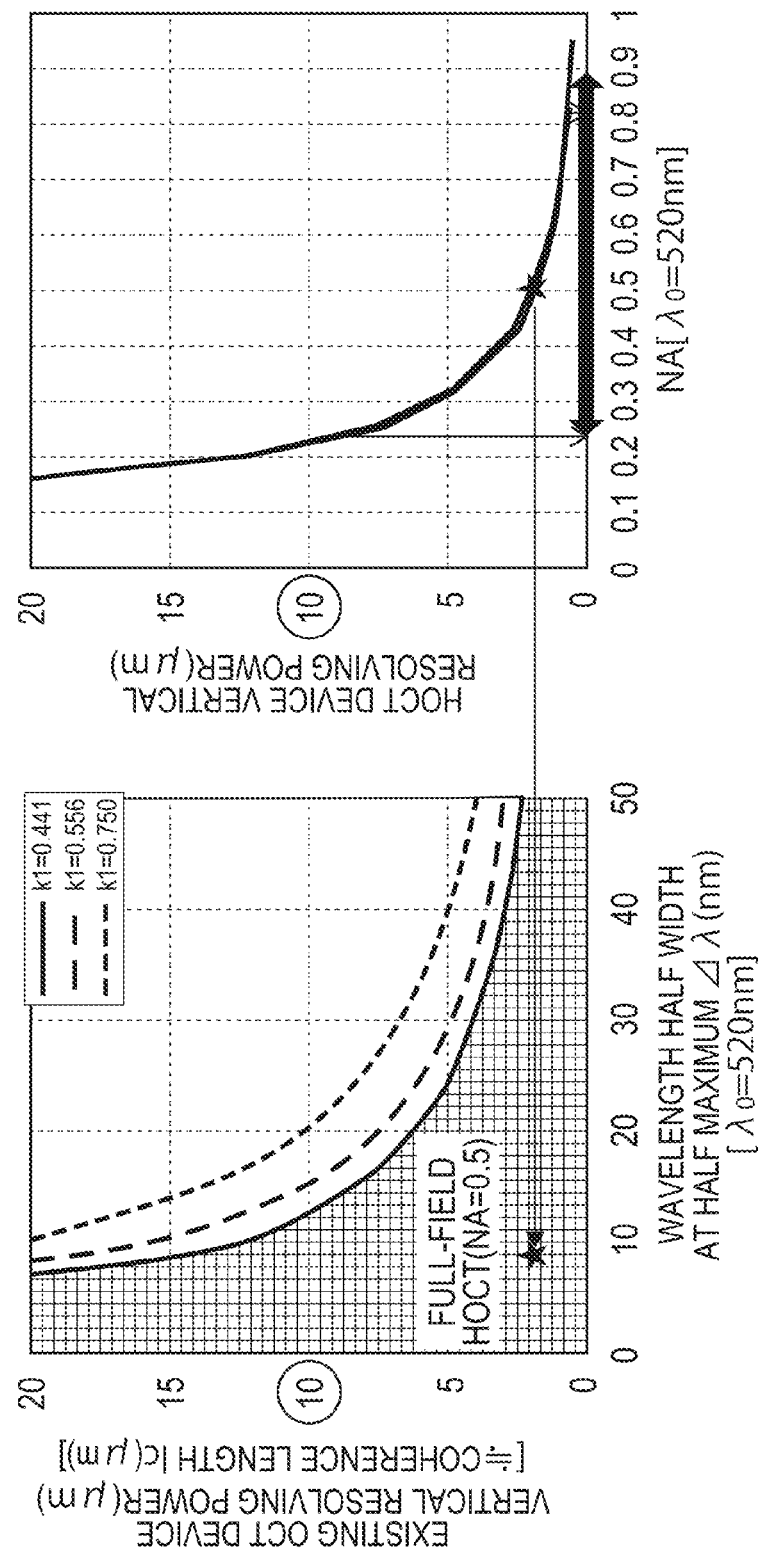
FIG. 20 are vertical resolving power comparison diagrams of the HOCT of the third embodiment and the conventional OCT.

FIG. 20 is diagrams comparatively showing the vertical resolving powers of the HOCT of the present embodiment and the conventional OCT. In addition, the mark * in the drawing indicates the situation which has been realized by the present embodiment. When attention is paid to the mark * in FIG. 20, in the present embodiment, the vertical resolving power of 1.84 μm (the full width at half maximum FWHM of the light spot in the optical axis (z) direction) realization of which is difficult for the conventional OCT could be attained by using the semiconductor laser which achieves the wavelength λ=520 μm and the wavelength half width at half maximum=10 nm, and the objective lens of NA=0.5.

Figure 21:
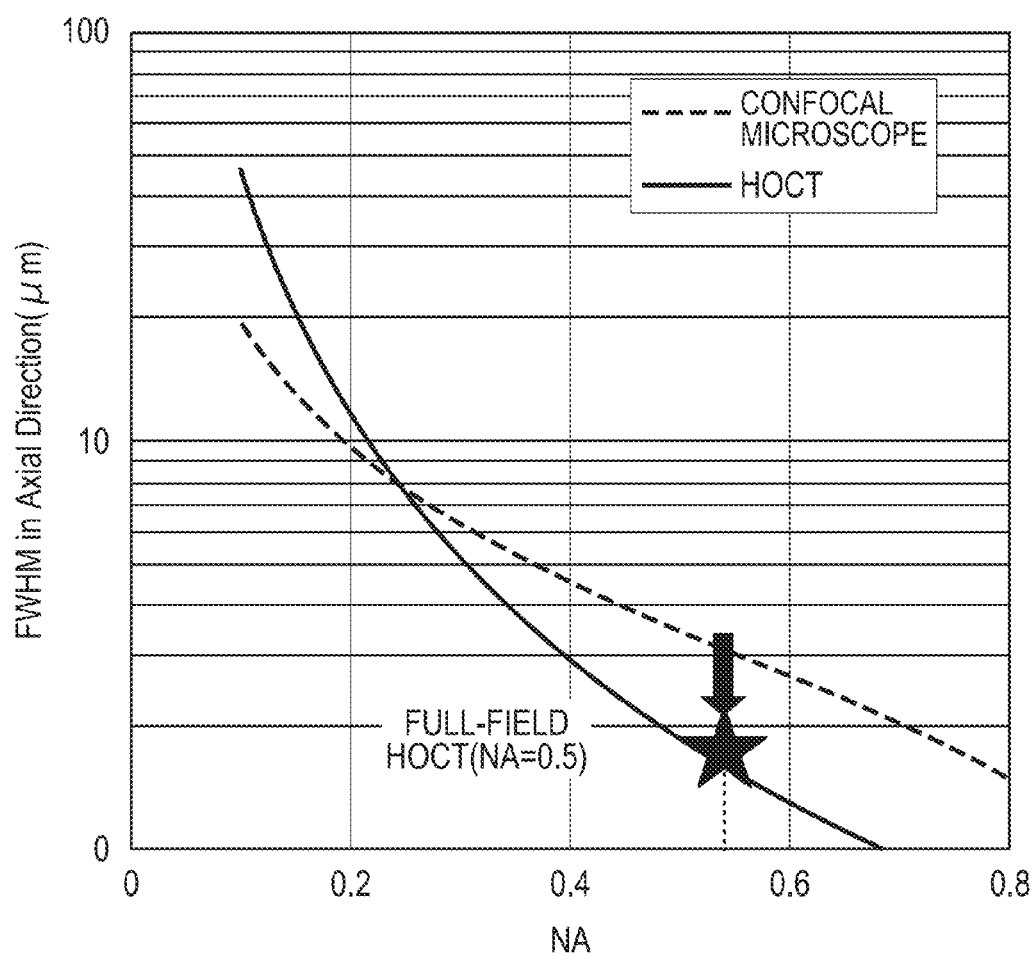
FIG. 21 are vertical resolving power comparison diagrams of the HOCT of the third embodiment and the confocal microscope.

FIG. 21 is a diagram comparatively showing the vertical resolving powers of the HOCT of the present embodiment and the confocal microscope. Here, when attention is paid to the mark * in FIG. 21, in the present embodiment, the vertical resolving power of 1.84 μm (the full width at half maximum FWHM of the light spot in the optical axis (z) direction) realization of which is difficult even for the confocal microscope could be attained by the semiconductor laser which achieves the wavelength λ=520 μm, and the objective lens of NA=0.5, the CCD of the detector size S per pixel=100 μm² (10 μm □), and the HOCT optical system which achieves the detection magnification M=4.

Fourth Embodiment

Figure 22:
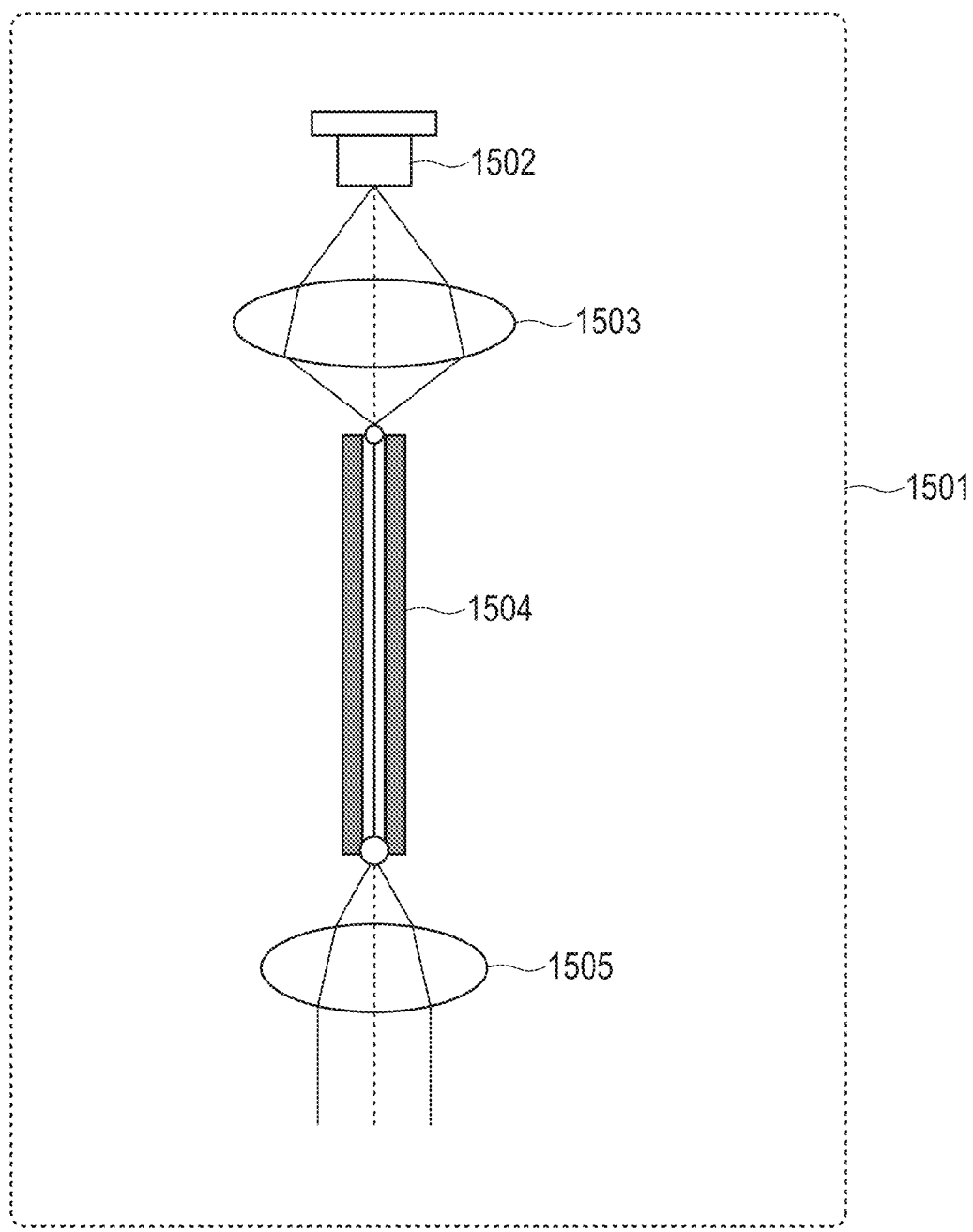
FIG. 22 is a block diagram of a light source unit.

Although, in the present embodiment, it was configured to realize the full-field type one similarly to the third embodiment, it is different in the point that the semiconductor laser (LD) was used for the light source. FIG. 22 is a block diagram of a light source unit in an optical tomographic observation device of the present embodiment. In the present embodiment, in a light source unit 1501, the LD which is a point light source of 2 μm in emitted spot diameter and which is the wavelength=520 nm and the wavelength half width at half maximum≤1 nm was used as a light source 1502. Incidentally, if it is the point light source, the gas laser, the solid-state laser and so forth can also be used. Although these light sources are increased in size and power consumption, there are such advantages that the output can be made large, the wavelength half width at half maximum can be made small and so forth.

In order to full-field this point light source, it is necessary to convert it into the surface light source. However, if the beam expander used in the third embodiment is applied as it is, the magnification for enlargement which becomes necessary will amount to ×100 and it will no longer have the realistic size of the optical system. Accordingly, in the present embodiment, it was configured to couple laser light emitted from the light source 1502 to an optical waveguide 1504 using a coupling lens 1503. At this time, the light spot which is approximate to a core diameter of the light waveguide, that is, the surface light source can be obtained on an outgoing end surface of the optical waveguide 1504. Since this light spot turns to diverging light having a divergence angle according to a core/clad refractive index ratio of the optical waveguide in the air, it was configured to make it into the collimated light by using a collimate lens 1505 and to guide it to the optical observation unit. By configuring it in this way, such advantages arose that (1) simple designing of the surface light source becomes possible in the design (the core diameter, the core/clad refractive index ratio) of the optical waveguide and (2) an enlargement/reduction ratio of the surface light source can be adjusted by selecting the collimate lens and the objective lens. In particular, since the size of the point light source such as the semiconductor laser and on forth is generally about several μm, in order to illuminate the visual field of, for example, 500 to 600 μm, it is necessary to increase the spot size by 100 or more times and enlargement of the optical system is induced by spot enlargement by a simple combination of the plurality of lenses. On the other hand, in the present embodiment, it is once increased by several-ten times in the optical waveguide and then the spot size adjustment of several times may be performed by the collimate lens and the objective lens. In the present embodiment, a multi-mode fiber of 0.22 in NA and 200 μm in core diameter was used as the optical waveguide 1504. Although the light having the divergence angle (0.22 in NA) is outgone from the end surface of the optical waveguide 1504, the illumination light having the beam diameter of 200 μm could be formed similarly to the third embodiment by making it into the collimated light by the collimate lens 1505 of 0.5 in NA which is larger than NA thereof.

Other fundamental configurations and operations of the present embodiment are the same as those of the third embodiment. In the present embodiment, since simple surface illumination can be realized by the light source enlargement unit even when the semiconductor laser which is the point light source is used, the full-field OCT which can be speeded up could be realized. In addition, since the semiconductor laser can be used, it is possible to relax the component adjustment accuracy of the interference optical system down to mm order by making use of the long coherence length. This contributes to cost reduction of the optical tomographic device that uses the HOCT.

Incidentally, the present invention is not limited to the abovementioned embodiments and various altered examples are included therein. For example, the abovementioned embodiments have been described in detail in order to describe the present invention so as to be easily understandable and are not necessarily limited to those possessing all of the configurations which have been described. In addition, it is possible to replace part of a configuration of a certain embodiment with a configuration of another embodiment, and it is also possible to add a configuration of another embodiment to a configuration of a certain embodiment. In addition, it is possible to perform addition, deletion, and replacement of another configuration in regard to part of a configuration of each embodiment.

INDUSTRIAL APPLICABILITY

According to the present invention, it becomes possible to provide the interference type optical tomographic observation device which can output a stable amplified signal and has the high vertical resolving power, not influenced by various characteristic variations which would occur in the actual optical system. In addition, the interference type full-field optical tomographic observation device which can be speeded up while having the high vertical resolving power can be provided.

REFERENCE SIGNS LIST

601: light source unit, 602: optical observation head unit, 603: photo-detection unit, 604: control unit, 605: signal processing unit, 606: information input/output unit, 615: light source, 620; actuator, 621: objective lens, 622: sample, 624: light spot, 626: mirror, 630, 635: Wollaston prism, 631, 636: differential detector, 1116: phase modulation plate, 1117: photodetector, 1504: optical waveguide

The invention claimed is:

1. An optical tomographic observation device, comprising:
    a light source which emits laser light;
    an optical system provided with an optical element which splits a light beam emitted from the light source into a first light beam and a second light beam, an objective optical element which condenses the first light beam onto a sample and irradiates it with the first light beam, and receives reflected light reflected from the sample as signal light, a reflection element which is provided in an optical path of the second light beam and reflects the second light beam as reference light, and an optical element which multiplexes the signal light and the reference light;
    a plurality of photodetectors;
    an interference optical system which guides the multiplexed light beam to the plurality of photodetectors and makes the signal light interfere with the reference light on each detector in a relation that they are mutually different in phase;
    a control unit which controls a condensing position of the first beam with which the sample is to be irradiated; and
    an arithmetic operation circuit which performs an arithmetic operation of making outputs from the plurality of photodetectors into inputs and acquires a detection signal corresponding to the signal light,
    wherein when $\lambda$ is a wavelength of the laser light, $\Delta\lambda$ is a wavelength half width at half maximum, NA is a numerical aperture of the objective optical element, S is an effective area of the photodetector, and M is a detection magnification of a detection surface relative to a condensing surface, the following formula is satisfied $$\frac{1}{NA^2} \le \frac{k_1}{0.886} \frac{\lambda}{\Delta\lambda}$$

$$\frac{\lambda}{\left(NA\sqrt{1-NA^2}\right)} \le 0.901\sqrt{\frac{S}{M^2}}$$

$$0.441 \le k_1 \le 0.750.$$

2. The optical tomographic observation device according to claim 1, satisfying 400≤$\lambda$≤850 (nm)

0≤$\Delta\lambda$≤25 (mm)

0.25≤NA≤0.9

4≤S≤100 ($\mu m^2$)

2≤M≤10

(however, 2≤$\sqrt{(S/M^2)}$≤10 ($\mu m$)).

3. The optical tomographic observation device according to claim 1, wherein the objective optical element is an objective lens, and the control unit moves the objective lens in an optical axis direction in order to scan a condensing position by the objective lens.

4. The optical tomographic observation device according to claim 1,
    wherein the number of the photodetectors is four, and
    a pair of streaks of interference light that interference phases of the signal light and the reference light on the four photodetectors are mutually different by an integral multiple of almost 90 degrees, and the interference phases of the signal light and the reference light are mutually different by almost 180 degrees is detected by a differential detector.

5. The optical tomographic observation device according to claim 1, wherein the light source is any of a gas laser, a solid-state laser, a semiconductor laser and a super-luminescent diode of which the wavelength half width at half maximum is 0≤$\Delta\lambda$≤25 (nm).

6. An optical tomographic observation device, comprising:
    a light source which emits laser light;
    an optical system provided with an optical element which splits a light beam emitted from the light source into a first light beam and a second light beam, an objective optical element which condenses the first light beam onto a sample and irradiates it with the first light beam as surface illumination, and receives reflected light reflected from the sample as signal light, a reflection element which is provided in an optical path of the second light beam and reflects the second light beam as reference light, and an optical element which multiplexes the signal light and the reference light;

a photodetector provided with a plurality of two-dimensionally arranged photo-detection elements;

an interference optical system which guides the multiplexed light beam to the photodetector and makes the signal light interfere with the reference light on the plurality of photo-detection elements of the photodetector in a relation that they are mutually different in phase;

a control unit which controls a condensing position of the first beam with which the sample is to be irradiated; and an arithmetic operation circuit which performs an arithmetic operation of making outputs from the plurality of photodetectors into inputs and acquires a detection signal corresponding to the signal light, wherein when $\lambda$ is a wavelength of the laser light, $\Delta\lambda$ is a wavelength half width at half maximum, NA is a numerical aperture of the objective optical element, S is an area of the detection element on the photodetector, and M is a detection magnification of a detection surface relative to a condensing surface, the following formula is satisfied $$\frac{1}{NA^2} \le \frac{k_1}{0.886}\frac{\lambda}{\Delta\lambda}$$

$$\frac{\lambda}{(NA\sqrt{1-NA^2})} \le 0.901\sqrt{\frac{S}{M^2}}$$

$$0.441 \le k_1 \le 0.750.$$

7. The optical tomographic observation device according to claim 6, wherein the NA satisfies $$0.250 \le NA \le 0.574.$$

8. The optical tomographic observation device according to claim 6, wherein the number of the photodetector is one, and the photo-detection elements are combined together for every adjacent 2×2 ones, the photodetector has a phase modulation plate arranged in front of a detection surface, the phase modulation plate has a function of modulating the phase of incident light such that a pair of streaks of interference light that interference phases of the signal light and the reference light are mutually different by an integer multiple of almost 90 degrees and the interference phases of the signal light and the reference light are mutually different by almost 180 degrees relative to the 2×2 photo-detection elements is incident upon the every adjacent 2×2 photo-detection elements, and when (O×P) is a number of the photo-detection elements which configure the photodetector and $D_{(x,y)}$ is a signal acquired by the photo-detection elements arranged at positions (x, y) on the photodetector, the following formula is satisfied $$D_{(x,y)}=D_{(2o,2p)}=I_1=\tfrac{1}{4}|E_{sig}+E_{ref}|^2$$

$$D_{(x,y)}=D_{(2o+1,2p)}=Q_1=\tfrac{1}{4}|E_{sig}+iE_{ref}|^2$$

$$D_{(x,y)}=D_{(2o,2p+1)}=Q_2=\tfrac{1}{4}|E_{sig}-iE_{ref}|^2$$

$$D_{(x,y)}=D_{(2o+1,2p+1)}=I_2=\tfrac{1}{4}|E_{sig}-E_{ref}|^2$$

However, $O<o \le O/2$, $O<p \le P/2$ (any of o, p, O, P is an integer) and i is an imaginary number.

9. The optical tomographic observation device according to claim 8, wherein a detection signal $Sig_{(2o,2p)}$ at positions (2o, 2p) obtained by the optical tomographic observation device is such that a pair of streaks of interference light that phases are mutually different by almost every 180 degrees is differentially detected so as to satisfy the following formula for every pair of the 2×2 circuits $$Sig_{(2o,2p)}^2=(D_{(2o,2p)}-D_{(2o+1,2p+1)})^2+(D_{(2o+1,2p)}-D_{(2o,2p+1)})^2=(I_1-I_2)^2+(Q_1-Q_2)^2=|E_{sig}|^2|E_{ref}|^2.$$

10. The optical tomographic observation device according to claim 6, wherein the light source is provided with any of a gas laser, a solid-state laser, a semiconductor laser, a superluminescent diode, a light emitting diode, a surface emission semiconductor laser and an electroluminescence element of which the wavelength half width at half maximum thereof is $0 \le \Delta\lambda \le 25$ (nm), and a light source enlargement unit, and the light source enlargement unit performs surface irradiation on the sample by making the size of an illumination spot on a condensing surface of an observation sample that the light source forms larger than the size which can be detected on the entire surface of the photodetector.

11. The optical tomographic observation device according to claim 10, wherein the light source enlargement unit has an optical waveguide and a collimate lens, and makes a light spot emitted from the light source which has been coupled to the optical waveguide into collimated light by the collimator lens, condenses the light spot by the objective optical element and thereby enlargedly projects the light spot on an outgoing end surface of the optical waveguide onto a condensing surface of the sample in accordance with lateral magnifications of the collimator lens and the objective optical element.

12. The optical tomographic observation device according to claim 10, wherein the light source enlargement unit is a beam expander configured by a plurality of lenses, and enlargedly projects the light spot on an outgoing end surface of the light source onto the condensing surface of the sample in accordance with a lateral magnification of the beam expander.

* * * * *